(12) United States Patent
Shluzas

(10) Patent No.: US 6,648,888 B1
(45) Date of Patent: Nov. 18, 2003

(54) SURGICAL INSTRUMENT FOR MOVING A VERTEBRA

(75) Inventor: Alan E. Shluzas, Millis, MA (US)

(73) Assignee: Endius Incorporated, Plainville, MA (US)

(*) Notice: Subject to any disclaimer, the term of this patent is extended or adjusted under 35 U.S.C. 154(b) by 0 days.

(21) Appl. No.: 10/236,713

(22) Filed: Sep. 6, 2002

(51) Int. Cl.$^7$ .......................... A61B 17/56; A61B 17/58
(52) U.S. Cl. .......................... 606/61; 606/90
(58) Field of Search .............. 606/60, 61, 72, 606/73, 86, 99, 104, 90, 96

(56) References Cited

U.S. PATENT DOCUMENTS

| | | | |
|---|---|---|---|
| 4,611,581 A | | 9/1986 | Steffee |
| 5,020,519 A | * | 6/1991 | Hayes et al. ................. 606/237 |
| 5,375,956 A | * | 12/1994 | Pennig ......................... 411/389 |
| 5,720,751 A | * | 2/1998 | Jackson ........................ 606/86 |
| 5,899,901 A | | 5/1999 | Middleton |
| 5,910,141 A | * | 6/1999 | Morrison et al. ............. 606/61 |
| 6,123,707 A | | 9/2000 | Wagner |
| 6,251,111 B1 | | 6/2001 | Barker et al. |
| 6,379,356 B1 | * | 4/2002 | Jackson ........................ 606/61 |
| 6,440,133 B1 | | 8/2002 | Beale et al. |
| 2003/0023243 A1 | * | 1/2003 | Biedermann et al. ......... 606/73 |

OTHER PUBLICATIONS

Medtronic Sofamor Danek presentation materials (7, 16□22 pages) entitled CD Horizon® Spinal System Surgical Technique, dated 2001.

Synthes® Spine presentation materials (6 pages) entitled Click X™ Spondylolisthesis System, dated 2001.

Two photocopies of an actual instrument called the "M8 Rod Reducer". The M8 screw is a polyaxial top loading screw. This M8 Rod Reducer grabs the housing of the screw and permits the screwdriver and cap screw to pass down through it..

\* cited by examiner

*Primary Examiner*—Pedro Philogene
*Assistant Examiner*—David A Bonderer
(74) *Attorney, Agent, or Firm*—Tarolli, Sundheim, Covell & Tummino L.L.P.

(57) ABSTRACT

A surgical instrument comprises a first device including an actuatable clamp for clamping on a fastener fixed to a first bone portion and a carriage that is movable relative to the clamp when subjected to a predetermined axial load. A second device includes a portion adapted for threaded engagement with the carriage and an end portion for supporting a member for securing a rod connected to a second bone portion to the fastener. Relative rotation between the first and second devices causes relative axial movement between the second device and the carriage of the first-device. The carriage is stationary relative to the clamp of the first device when a force necessary to produce relative movement between the first and second bone portions is below the predetermined axial load so that relative rotation between the first and second devices first bone portion relative to the second bone portion.

32 Claims, 13 Drawing Sheets

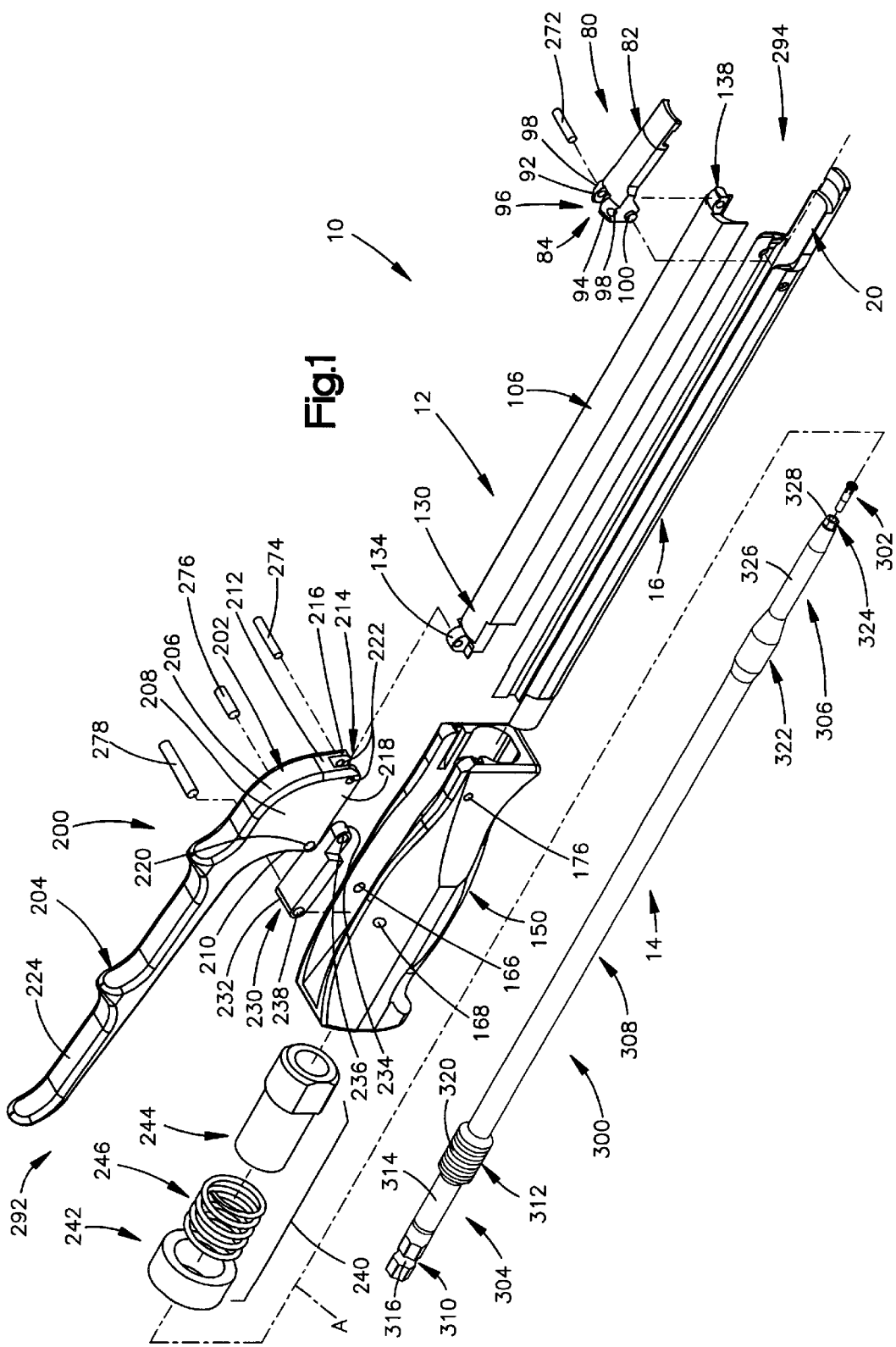

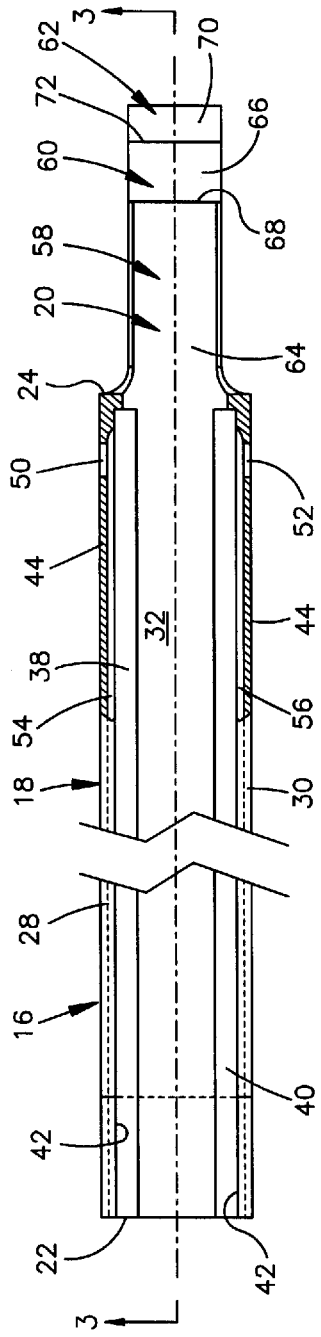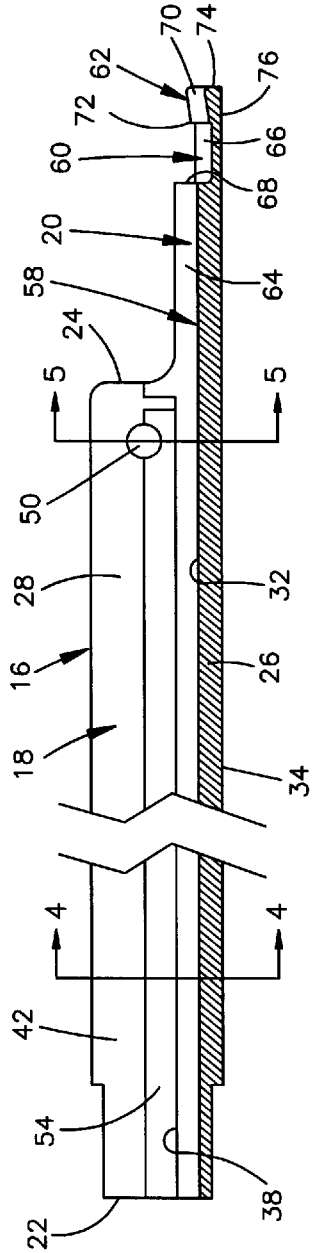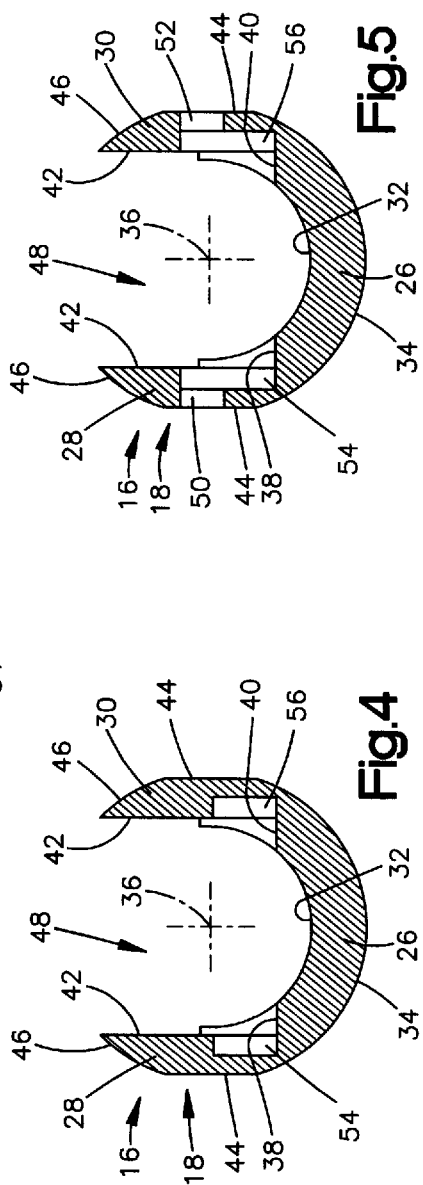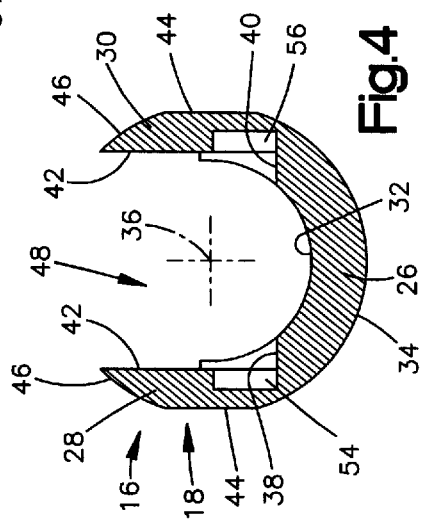

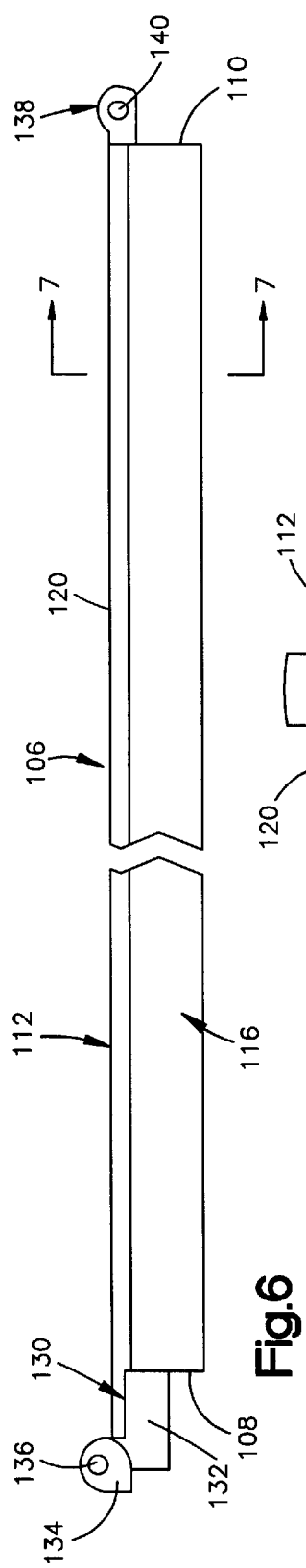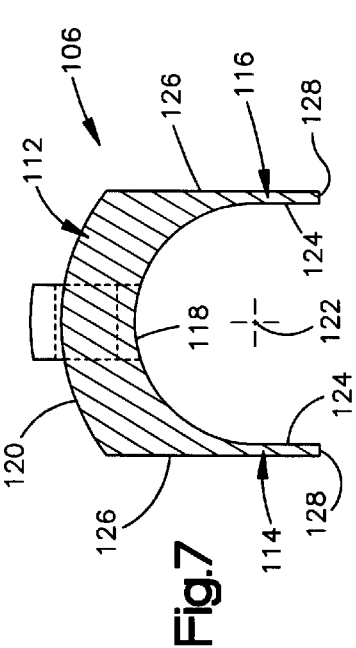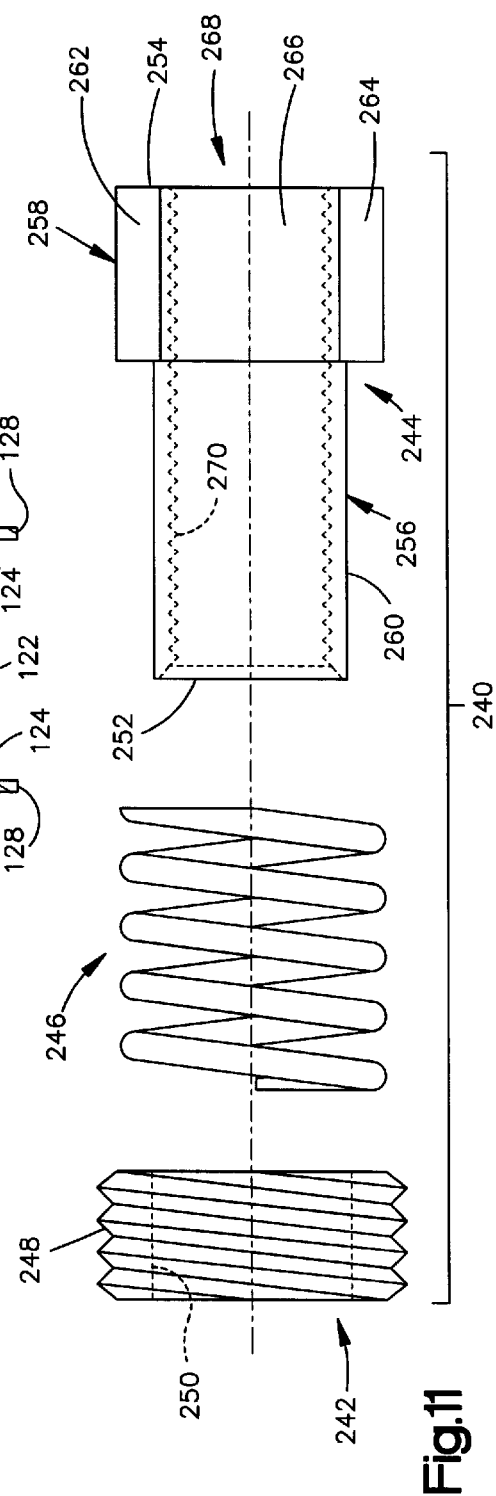

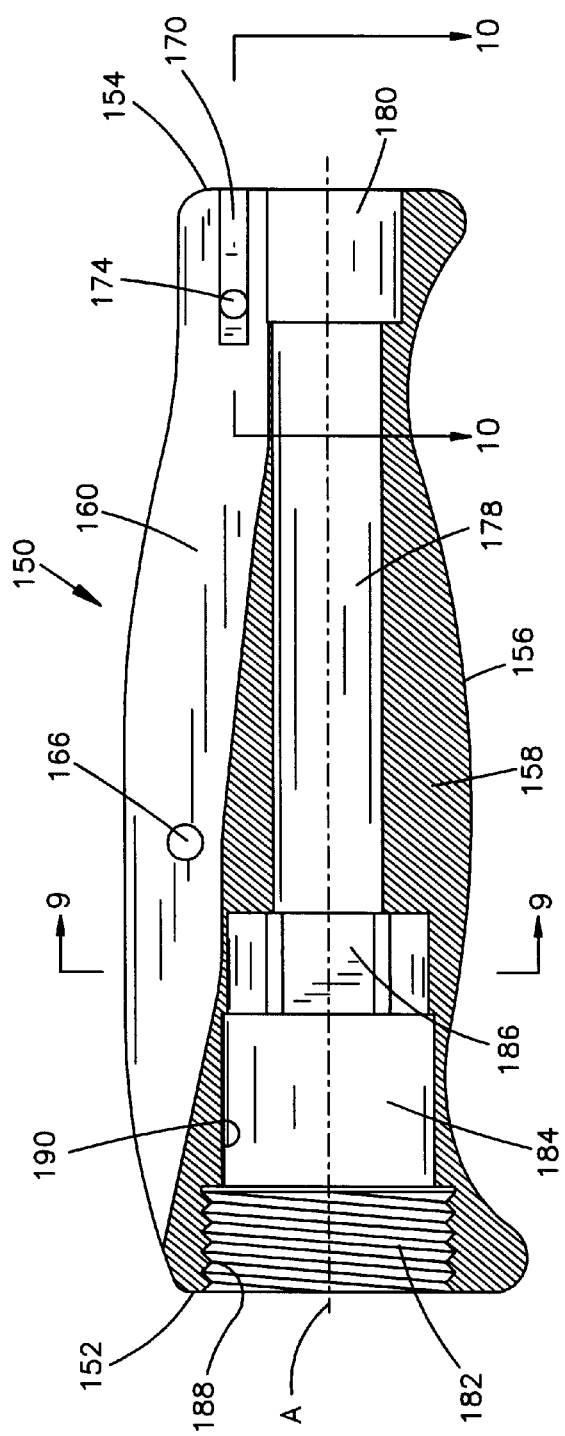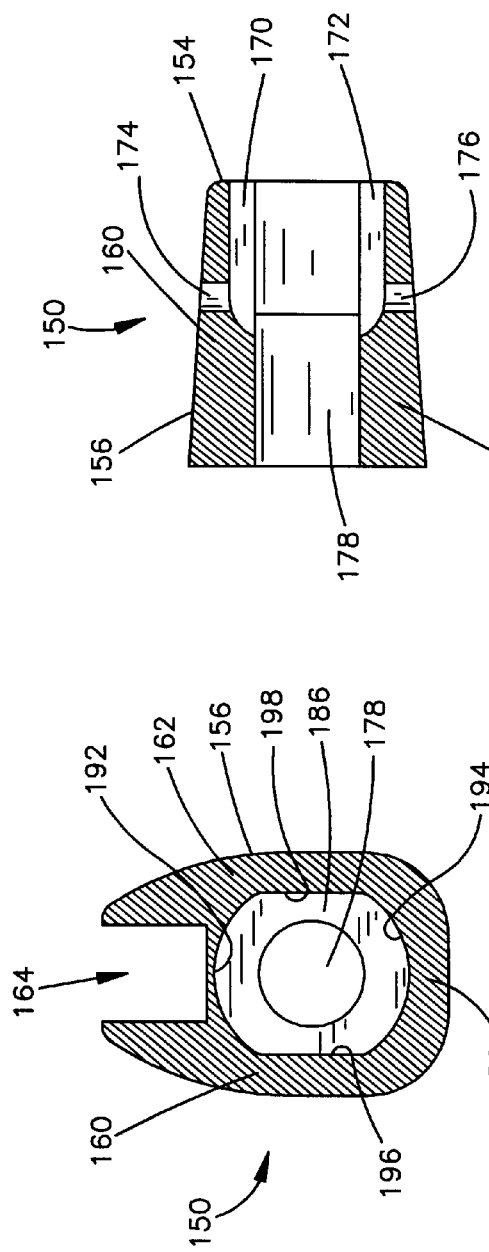

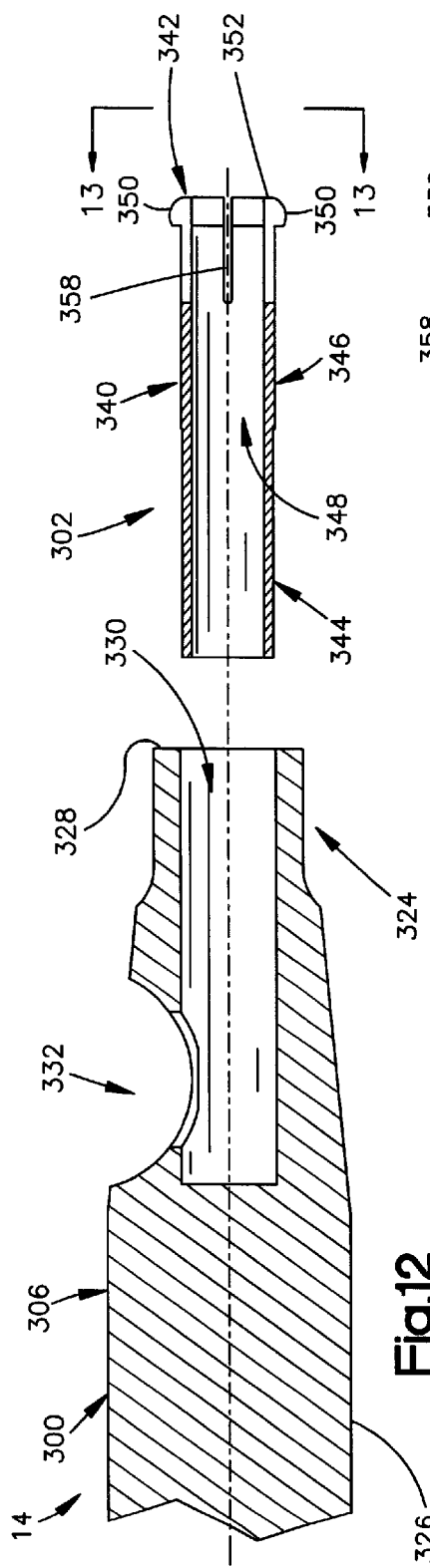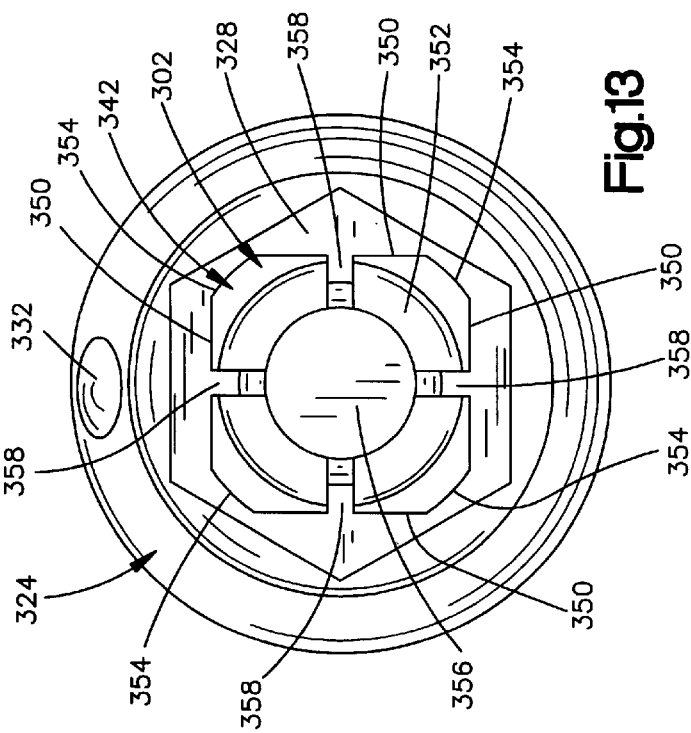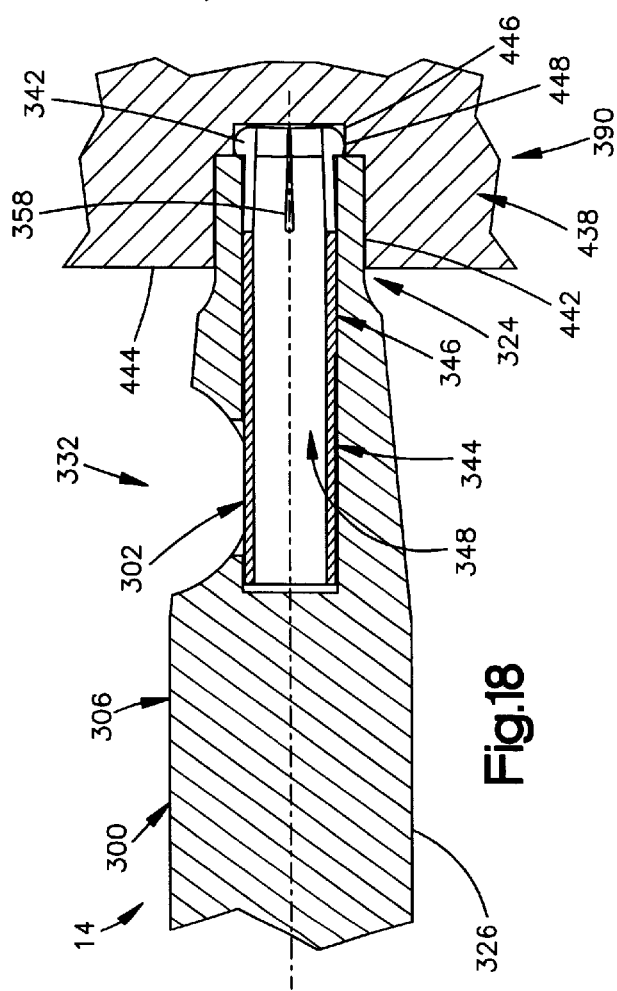

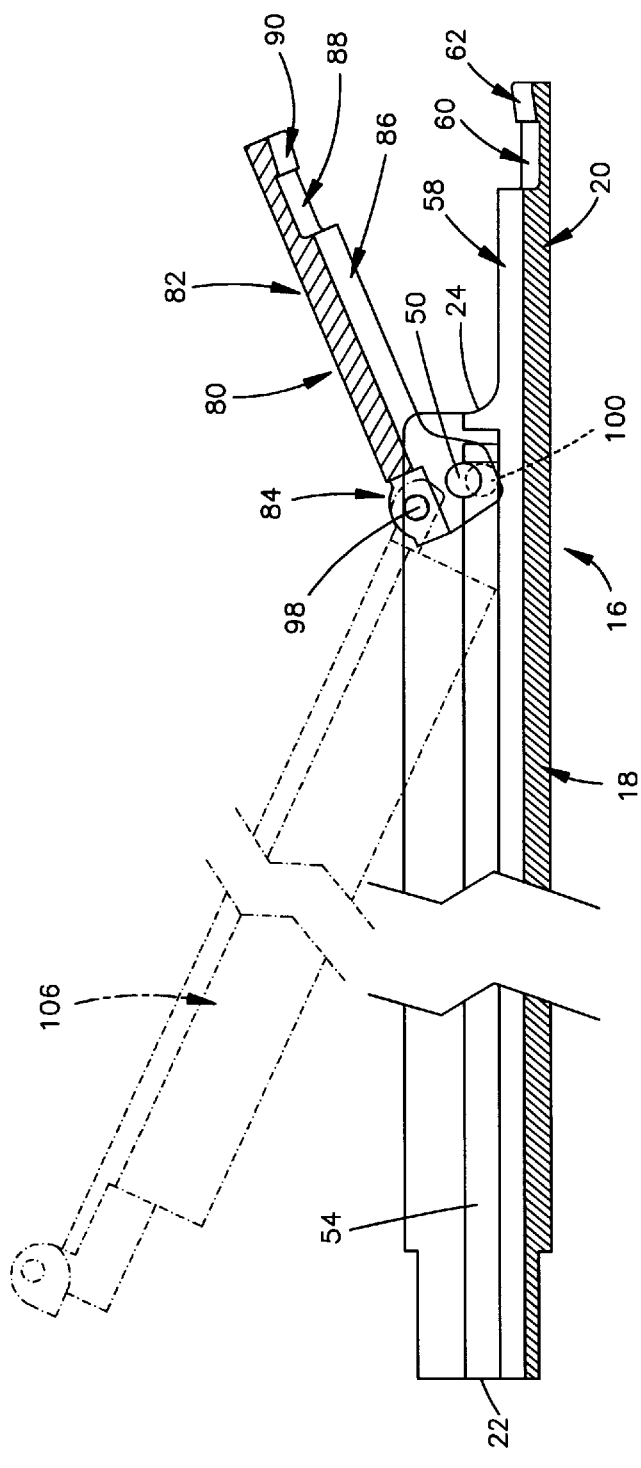
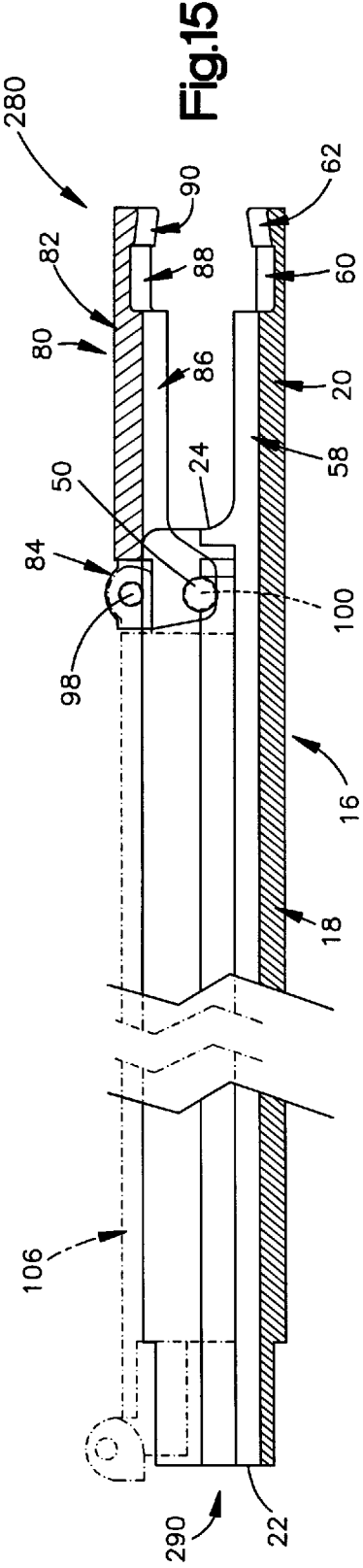
Fig.14
Fig.15

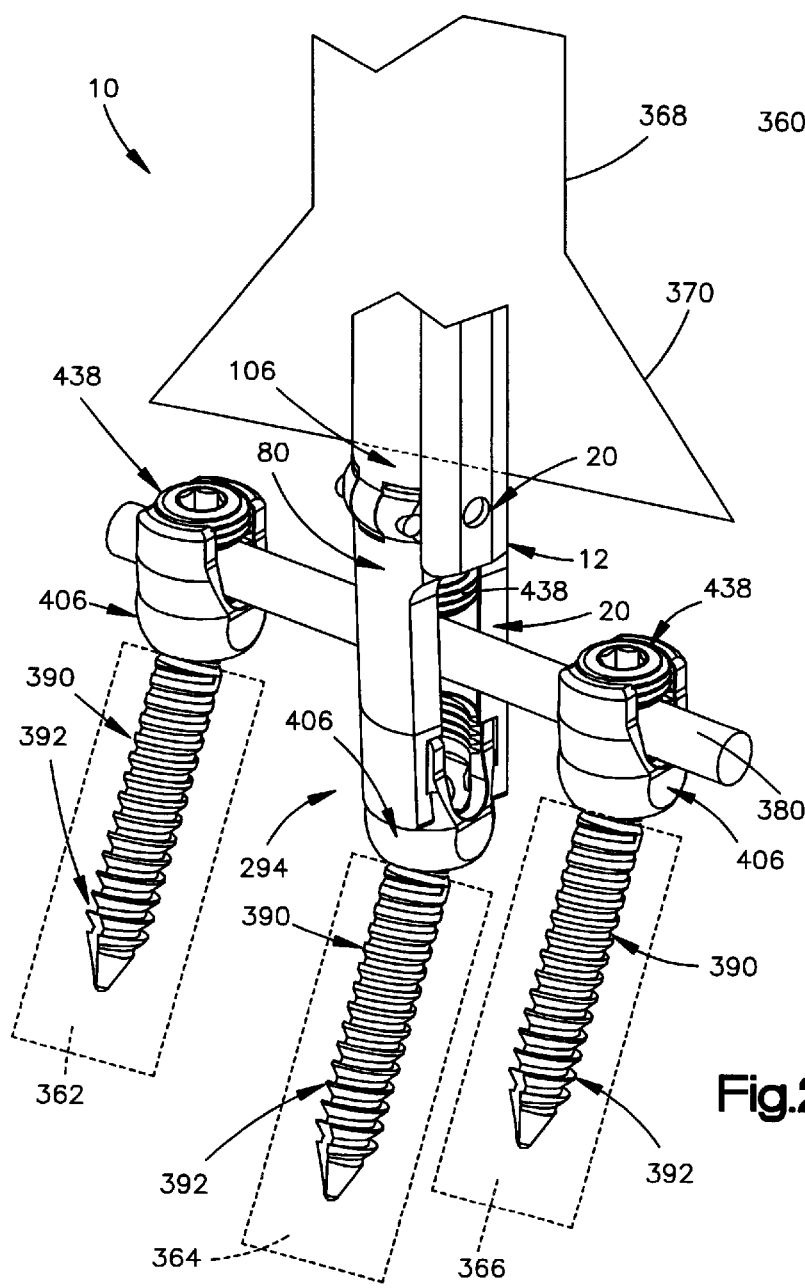

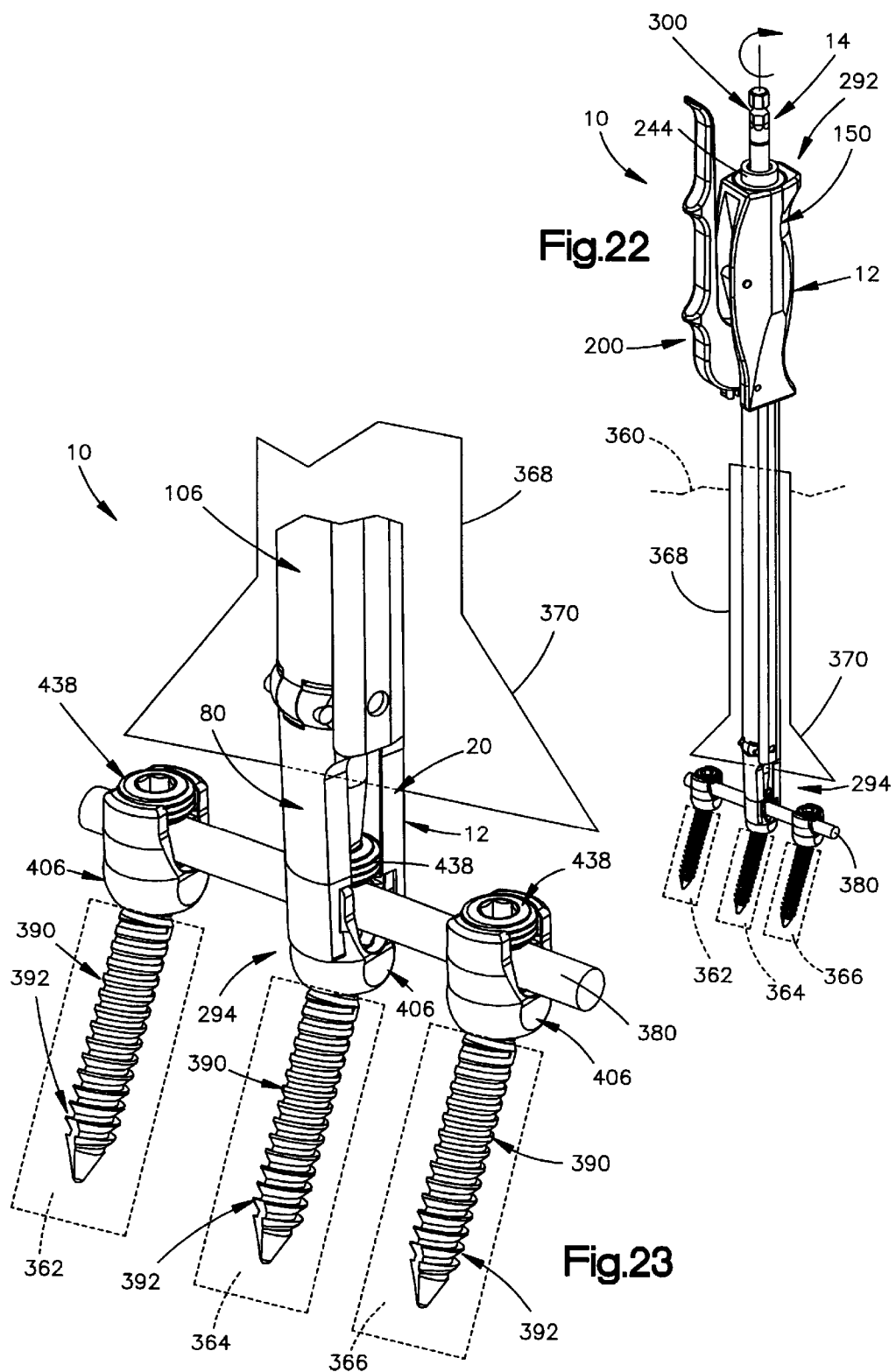

SURGICAL INSTRUMENT FOR MOVING A VERTEBRA

TECHNICAL FIELD

The present invention relates to a surgical instrument for moving a bone portion relative to another bone portion. More particularly, the present invention relates to a surgical instrument for moving a vertebra relative to another vertebra.

BACKGROUND OF THE INVENTION

It is known to secure a fixation rod relative to a first vertebra for supporting a second vertebra that has moved away from, or slipped relative to, a desired position. An implant is attached to the second vertebra. The second vertebra is moved relative to the first vertebra so that the implant may be secured to the fixation rod.

A conventional surgical instrument for moving the second vertebra relative to the first vertebra for securing the implant to the fixation rod includes an instrument for attaching to the implant in the second vertebra. An outwardly extending flange of the instrument supports a corkscrew device. When supported in the flange, a distal end of the corkscrew device may be driven against the fixation rod. Rotation of the corkscrew device relative to the instrument drives the fixation rod into the implant in the second vertebra. An implant plug is introduced into the implant through a cannulation in the instrument. The implant plug secures the implant to the rod so that the second vertebra becomes fixed relative to the first vertebra.

SUMMARY OF THE INVENTION

The present invention relates to a surgical instrument for moving a first bone portion relative to a second bone portion. The surgical instrument comprises first and second devices. The first device includes an actuatable clamp for clamping on a fastener fixed to the first bone portion and a threaded carriage that is movable axially relative to the clamp in a direction away from the first bone portion when subjected to a predetermined axial load. The second device includes a threaded portion adapted for threaded engagement with the carriage of the first device and an end portion for supporting a member which engages the fastener fixed to the first bone portion and secures a rod connected to the second bone portion to the fastener. The end portion is adapted for pressing the member against the rod. Relative rotation between the first and second devices during threaded engagement of the carriage of the first device and the threaded portion of the second device causes relative axial movement between the second device and the carriage of the first device. The carriage is stationary relative to the clamp of the first device when a force necessary to produce relative movement between the first and second bone portions is below the predetermined axial load so that relative rotation between the first and second devices moves the clamp and the fastener fixed to the first bone portion and the first bone portion relative to the second bone portion and relative to the rod.

According to another aspect, the present invention relates to a surgical instrument for moving a first bone portion of a body relative to a second bone portion of the body. The surgical instrument comprises a cannula for forming a passage into the body and for defining an operative space adjacent the first and second bone portions. A first device is extendable through the passage formed by the cannula. The first device includes an actuatable clamp for clamping on a fastener fixed to the first bone portion and a threaded carriage that is movable axially relative to the clamp in a direction away from the first bone portion when subjected to a predetermined axial load. A second device is also extendable through the passage formed by the cannula. The second device includes a threaded portion adapted for threaded engagement with the carriage of the first device and an end portion for supporting a member which engages the fastener fixed to the first bone portion and secures a rod connected to the second bone portion to the fastener. The end portion is adapted for pressing the member against the rod. Relative rotation between the first and second devices during threaded engagement of the carriage of the first device and the threaded portion of the second device causes relative axial movement between the second device and the carriage of the first device. The carriage is stationary relative to the clamp of the first device when a force necessary to produce relative movement between the first and second bone portions is below the predetermined axial load so that relative rotation between the first and second devices moves the clamp and the fastener fixed to the first bone portion and the first bone portion relative to the second bone portion and relative to the rod.

According to yet another aspect, the present invention relates to a surgical instrument for threadedly connecting a member and a fastener. The surgical instrument comprises a first device and a second device. The first device includes an actuatable clamp for clamping on the fastener and a threaded carriage that is movable axially relative to the clamp in a direction away from the fastener when subjected to a predetermined axial load. The second device includes a threaded portion adapted for threaded engagement with the carriage of the first device and an end portion for supporting the member to be threadedly connected to the fastener. Relative rotation between the first and second devices during threaded engagement of the carriage of the first device and the threaded portion of the second device causes relative axial movement between the second device and the carriage of the first device. The carriage moves axially away from the fastener that is clamped by the clamp of the first device when a force necessary to threadedly connect the member that is supported on the end portion of the second device and the fastener exceeds the predetermined axial load so that the member is rotated relative to the fastener but is not moved axially relative to the fastener in response to relative rotation between the first and second devices. The carriage is stationary relative to the fastener that is clamped by the clamp of the first device when the force necessary to threadedly connect the member that is supported on the end portion of the second device and the fastener is below the predetermined axial load so that relative rotation between the first and second devices results in the member being threadedly connected to the fastener.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is an exploded, perspective view of a surgical instrument constructed in accordance with the present invention;

FIG. 2 is a top plan view of a fixed shaft of a reduction device of the surgical instrument of FIG. 1;

FIG. 3 is a view taken along line 3—3 in FIG. 2;

FIG. 4 is a view taken along line 4—4 in FIG. 3;

FIG. 5 is a view taken along line 5—5 in FIG. 3;

FIG. 6 is an elevation view of an actuator shaft of the reduction device of the surgical instrument of FIG. 1;

FIG. 7 is a view taken along line 7—7 in FIG. 6;

FIG. 8 is a cross-sectional view of a fixed handle of the reduction device of the surgical instrument of FIG. 1;

FIG. 9 is a view taken along line 9—9 in FIG. 8;

FIG. 10 is a view taken along line 10—10 in FIG. 8;

FIG. 11 is an exploded view of a translation mechanism of the reduction device of the surgical instrument of FIG. 1;

FIG. 12 is an enlarged view of a driver spring and a second axial end of a driver of a drive device of the surgical instrument of FIG. 1;

FIG. 13 is a view taken along line 13—13 in FIG. 12;

FIG. 14 is a view illustrating the assembly of a pivotal jaw to the fixed shaft of the reduction device of the surgical instrument of FIG. 1;

FIG. 15 is a view illustrating the pivotal jaw attached to the fixed shaft of the reduction device of the surgical instrument of FIG. 1;

FIG. 18 illustrates a setscrew of the fastener of FIG. 17 held on the second axial end of the drive device of the surgical instrument of FIG. 1;

FIG. 19 illustrates the surgical instrument of FIG. 1 being used to move a vertebra;

FIG. 20 is an enlarged portion of FIG. 19;

FIG. 22 illustrates the surgical instrument of FIG. 1 inserting a setscrew into the fastener of FIG. 17 to secure a vertebra to a rod;

FIG. 23 is an enlarged portion of FIG. 22;

DETAILED DESCRIPTION OF THE INVENTION

Figure 16:
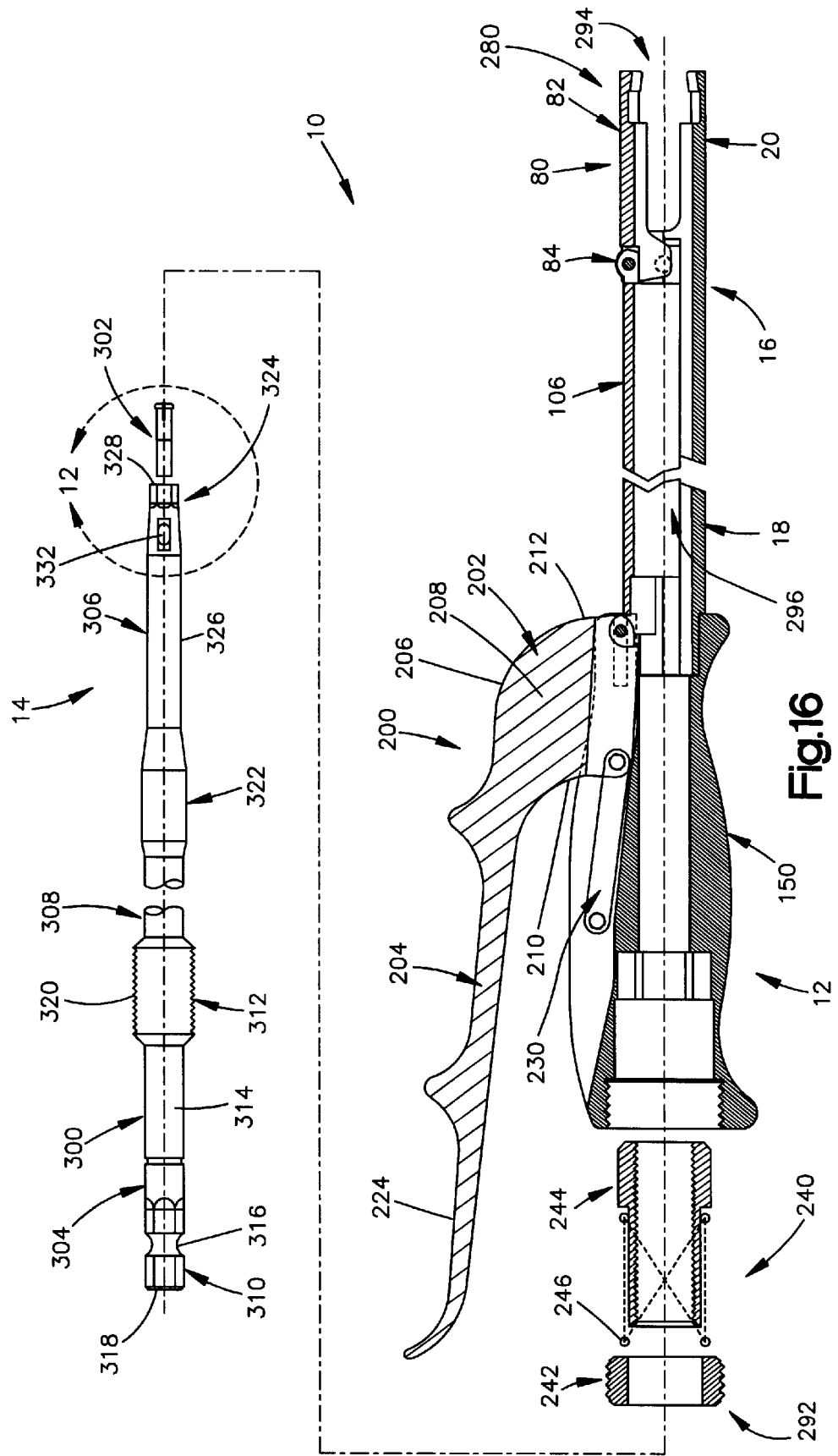
FIG. 16 is a side view, partially in section, of the surgical instrument of FIG. 1.

FIG. 1 is an exploded perspective view of a surgical instrument 10 constructed in accordance with the present invention. The surgical instrument 10 includes a reduction device 12 and a drive device 14.

The reduction device 12 includes a fixed shaft 16 that is formed from a biocompatible material. As shown in FIGS. 2–3, the fixed shaft 16 includes a main body portion 18 and a fixed jaw 20. The main body portion 18 extends axially between first and second axial ends 22 and 24, respectively. The main body portion 18 has a generally C-shaped cross-section, as shown in FIGS. 4–5. A bottom wall 26 and opposite first and second side walls 28 and 30, respectively, define the C-shaped cross-section of the main body portion 18 of the fixed shaft 16. The bottom wall 26 is arced and includes arcuate inner and outer surfaces 32 and 34, respectively. The inner surface 32 of the bottom wall 26 is centered at point 36. The bottom wall 26 terminates at first and second end surfaces 38 and 40, respectively. An arc length of the bottom wall of the fixed shaft is less than 180 degrees about point 36.

The first and second side walls 28 and 30 of the main body portion 18 of the fixed shaft 16 extend upwardly from the first and second end surfaces 38 and 40, respectively. The first and second side walls 28 and 30 include planar inner and outer surfaces 42 and 44, respectively, that are connected by curved end surfaces 46. The inner surface 42 of the first side wall 28 extends upwardly from a lateral midpoint of the first end surface 38 of the bottom wall 26 in a direction perpendicular to the first end surface 38. The outer surface 44 of the first side wall 28 extends parallel to the inner surface 42 and is contiguous with the outer surface 34 of the bottom wall 26. The inner surface 42 of the second side wall 30 extends upwardly from a lateral midpoint of the second end surface 40 of the bottom wall 26 in a direction perpendicular to the second end surface 40 of the bottom wall 26. The outer surface 44 of the second side wall 30 extends parallel to the inner surface 42 and is contiguous with the outer surface 34 of the bottom wall 26.

The arcuate inner surface 32 of the bottom wall 26 and the parallel inner surfaces 42. of the first and second side walls 28 and 30 collectively define a channel 48 (FIG. 4) in the main body portion 18 of the fixed shaft 16. An open top of the fixed shaft 16 leads into the channel 48.

First and second, coaxial through-holes 50 and 52, respectively, extend through the first and second side walls 28 and 30, respectively, adjacent the second axial end 24 of the main body portion 18 of the fixed shaft 16. The centers of the first and second through-holes 50 and 52 are aligned with point 36.

A slot 54 extends into the inner surface 42 of the first side wall 28 of the main body portion 18 of the fixed shaft 16 adjacent the first end surface 38 of the bottom wall 26. As shown in FIG. 3, the slot 54 in the first side wall 28 extends from the first axial end 22 of the main body portion 18 and terminates adjacent the first through-hole 50 near the second axial end 24 of the main body portion 18. The slot 54 is open on the first axial end 22 and is closed on the second axial end 24. The slot 54 partially intersects a lower portion of the first through-hole 50.

A slot 56 extends into the inner surface 42 of the second side wall 30 of the main body portion 18 adjacent the second end surface 40 of the bottom wall 26. As shown in FIG. 2, the slot 56 in the second side wall 30 extends from the first axial end 22 of the main body portion 18 and terminates adjacent the second through-hole 52 near the second axial end 24 of the main body portion 18. The slot 56 is open on the first axial end 22 and is closed on the second axial end 24. As shown in FIG. 2, the slot 56 partially intersects a lower portion of the second through-hole 52.

The fixed jaw 20 of the fixed shaft 16 extends axially outwardly of the bottom wall 26 of the main body portion 18 of the fixed shaft 16. The fixed jaw 20 includes a linking portion 58, a mouth portion 60 and a gripping portion 62.

As shown in FIGS. 2–3, an inner surface 64 of the linking portion 58 is arcuate and is formed by an axial extension of the inner surface 32 of the bottom wall 26. The mouth portion 60 of the fixed jaw 20 includes an arcuate inner surface 66. A shoulder 68 connects the inner surface 66 of the mouth portion 60 to the inner surface 64 of the linking portion 58. The gripping portion 62 includes a tapered inner surface 70. A shoulder 72 connects the inner surface 66 of the mouth portion 60 to the tapered inner surface 70 of the gripping portion 62. The tapered inner surface 70 of the gripping portion 62 widens near a terminal end 74 (FIG. 3) of the fixed jaw 20. An outer surface 76 of the fixed jaw 20 is arcuate. As shown in FIG. 3, the inner surface 66 of the mouth portion 60 is recessed, or nearer the outer surface 76 of the fixed jaw 20, relative to the inner surfaces 64 and 70 of the linking portion 58 and the gripping portion 62.

The reduction device 12 also includes a pivotal jaw 80 (FIG. 1). The pivotal jaw 80 includes a main body portion 82 and a pivotal portion 84. The main body portion 82 of the pivotal jaw 80 is a mirror image of the fixed jaw 20 of the fixed shaft 16. The pivotal jaw 80 also includes a linking portion 86, a mouth portion 88, and a gripping portion 90.

As shown in FIG. 1, the pivotal portion 84 of the pivotal jaw 80 includes first and second members 92 and 94, respectively, that are separated from one another by a central channel 96. Laterally extending through-holes 98 extend through an upper portion of the first and second members 92 and 94. A cylindrical pivot element 100 extends laterally outwardly of a lower portion of each of the first and second members 92 and 94.

The reduction device 12 also includes an actuator shaft 106, shown in detail in FIGS. 6–7. The actuator shaft 106 extends axially between first and second axial ends 108 and 110, respectively. An arcuate upper wall 112 and parallel side walls 114 and 116 define a generally C-shaped cross-section of the actuator shaft 106. The arcuate upper wall 112 includes inner and outer surfaces 118 and 120, respectively. The outer surface 120 of the upper wall 112 has a larger radius of curvature than the inner surface 118. The inner surface 118 is centered on point 122.

The side walls 114 and 116 of the actuator shaft 106 extend downwardly from the upper wall 112 beyond point 122. Each side wall 114 and 116 includes parallel inner and outer surfaces 124 and 126, respectively, and terminates at a lower end surface 128. The actuator shaft 106 has a width, measured laterally between the outer surfaces 126 of the side walls 114 and 116, that is sized to fit within the channel 48 of the fixed shaft 16 so that each side wall 114 and 116 of the actuator shaft 106 extends adjacent to an associated side wall 28 and 30 of the fixed shaft 16.

A first linking element 130 of the actuator shaft 106 extends axially outwardly of the first axial end 108 of the actuator shaft 106. The first linking element 130 includes an axial extension 132 and a linking member 134. The axial extension 132 extends axially outwardly of the first axial end 108 of the actuator shaft 106 and supports the linking member 134.

The linking member 134 extends axially outwardly of the axial extension 132. A laterally extending through-hole 134 extends through the linking member 134.

A second linking element 138 extends axially outwardly of the second axial end 110 of the actuator shaft 106. A laterally extending through-hole 140 extends through the second-linking element 138.

FIGS. 8–10 illustrated a fixed handle 150 of the reduction device 12. An axial length of the fixed handle 150 is defined between first and second axial ends 152 and 154, respectively. An outer surface 156 of the fixed handle 150 has a contour for receiving the palm of a hand. The outer surface 156 is defined by a curvilinear bottom wall 158 and opposite, arcuate side walls 160 and 162. An upper portion of the fixed handle 150, opposite the bottom wall 158, includes an axially extending channel 164 (FIG. 9), which is open at the top. A width of the channel 164 is defined between upper portions of the side walls 160 and 162 of the fixed handle 150.

First and second through-holes 166 and 168, respectively, (FIG. 1) extend through the upper portions of the side walls 160 and 162 to connect to the channel 164. The first and second through-holes 166 and 168 are located away from the first axial end 152 of the fixed handle 150 by approximately forty percent of the axial length of the fixed handle 150. The first and second through-holes 166 and 168 are coaxial with one another.

First and second axially extending slots 170 and 172 (FIG. 10), each of which is open to channel 164, extend into the upper portions of the side walls 160 and 162 adjacent the second axial end 154 of the fixed handle 150. Each of the first and second slots 170 and 172 is located radially inwardly, relative to axis A, than the first and second through-holes 166 and 168. As shown in FIGS. 8 and 10, the first slot 170 extends axially along the upper portion of the side wall 160 over an axial length of approximately fifteen percent of the fixed handle 150 before terminating. A through-hole 174 extends through the upper portion of the side wall 160 and intersects the first slot 170. As shown in FIG. 10, the second slot 172 extends axially along the upper portion of the side wall 162 over an axial length of approximately fifteen percent of the fixed handle 150 before terminating. A through-hole 176 extends through the upper portion of the side wall 162 and intersects the second slot 172.

A bore 178 extends axially through the fixed handle 150 from the first axial end 152 to the second axial end 154. The bore 178 includes a widened portion 180 (FIG. 8) adjacent the second axial end 154 of the fixed handle 150 for forming a seat for receiving the first axial end 22 of the main body portion 18 of the fixed shaft 16. The bore 178 widens into a series of wider diameter bores adjacent the first axial end 152 of the fixed handle 150. The series of wider diameter bores includes a first cylindrical bore 182, a second cylindrical bore 184, and a non-cylindrical bore 186.

The first cylindrical bore 182 is located immediately adjacent the first axial end 152 of the fixed handle 150. A cylindrical surface 188 that defines the first cylindrical bore 182 is threaded. The second cylindrical bore 184 is located immediately adjacent the first cylindrical bore 182 and has a smaller diameter than the first cylindrical bore 182. A cylindrical surface 190 defines the second cylindrical bore 184. The non-cylindrical bore 186 is located immediately adjacent the second cylindrical bore 184, opposite the first cylindrical bore 182. FIG. 9 is a cross-sectional view of the fixed handle 150 illustrating the non-cylindrical bore 186. The non-cylindrical bore 186 has an oblong shape that is defined by arcuate upper and lower surfaces 192 and 194, respectively, that are interconnected by parallel, planar surfaces 196 and 198. The planar surfaces 196 and 198 define a narrow portion of the oblong shaped non-cylindrical bore 186.

An actuation handle 200 (FIG. 1) of the reduction device 12 includes a main body portion 202 and an axially extending actuator portion 204. The main body portion 202 of the actuator handle 200 includes a rounded upper surface 206, a bottom surface (not shown), and planar first and second side surfaces 208. Only the second side surface 208 is shown in FIG. 1. The rounded upper surface 206 of the actuator handle 200 also includes first and second axial ends 210 and 212, respectively.

An axially extending channel 214 extends into the bottom surface of the actuator handle 200 to define first and second flanges 216 and 218, respectively. The first flange 216 extends between the first and second axial ends 210 and 212 of the main body portion 202 adjacent the first side surface. The second flange 218 extends between the first and second axial ends 210 and 212 of the main body portion 202 adjacent the second side surface 208. Coaxial through-holes 220 (only one of which is shown) extend through the first and second flanges 216 and 218 adjacent the first axial end 210 of the main body portion 202. Coaxial through-holes 222 extend through the first and second flanges 216 and 218 adjacent the second axial end 212 of the main body portion 202.

The actuator portion 204 of the actuator handle 200 extends axially outwardly of the first axial end 210 of the main body portion 202. The actuator portion 204 is an elongated rod having gripping features located on an upper surface 224.

An actuator linkage 230 (FIG. 1) of the reduction device 12 has a generally rectangular shape that is defined between first and second axial ends 232 and 234, respectively. Cutouts are removed from the second axial end 234 of the actuator linkage 230 so that a narrowed portion remains. A first through-hole 236 extends laterally through the narrowed portion of the actuator linkage 230 adjacent the second axial end 234. A second through-hole 238 extends laterally through the actuator linkage adjacent the first axial end 232.

The reduction device 12 also includes a translating mechanism 240. FIG. 11 shows an exploded side view of the translating mechanism 240. The translating mechanism 240 includes a locking cap 242, a carriage 244, and a spring 246.

The locking cap 242 is tubular and includes a threaded outer surface 248. The threaded outer surface 248 is sized to thread into the first cylindrical bore 182 of the fixed handle 150. An inner surface 250, shown by dashed lines in FIG. 11, of the locking cap 242 defines a bore having a diameter that is greater than the diameter of the bore 178 extending through the fixed handle 150.

The carriage 244 extends axially between first and second axial ends 252 and 254, respectively and includes a slider portion 256 and a head portion 258. The slider portion 256 extends from the first axial end 252 of the carriage 244 and has a cylindrical outer surface 260 that is dimensioned to be received in the bore of the locking cap 242. The head portion 258 extends from the second axial end 254 of the carriage 244 and has an oblong outer surface that includes arcuate upper and lower surfaces 262 and 264, respectively, that are connected by parallel, planar surfaces 266 (only one of which is shown). The head portion 258 of the carriage 244 is dimensioned to be received in the non-cylindrical bore 186 of the fixed handle 150 so that the planar surfaces 266 of the head portion 258 of the carriage 244 lie adjacent the planar surfaces 196 and 198 that define the non-cylindrical bore 186.

An axially extending bore 268 extends through the carriage 244 between the first and second axial ends 252 and 254. A threaded surface 270, shown by dashed lines in FIG. 11, defines the bore 268.

The spring 246 of the translating mechanism 240 urges the carriage 244 away from the locking cap 242. The spring 246 illustrated in FIG. 11 is a helical spring. The spring 246 has a predetermined spring constant. An inner diameter of the spring 246 is greater than the outer diameter of the slider portion 256 of the carriage 244. An outer diameter of the spring 246 is less than the diameter between the arcuate upper and lower surfaces 262 and 264 of the head portion 258 of the carriage 244 and is greater than the diameter of the inner surface 250 of the locking cap 242.

To assemble the reduction device 12, the second linking element 138 of the actuator shaft 106 is inserted into the central channel 96 of the pivotal portion 84 of the pivotal jaw 80 and the through-hole 140 in the second linking element 138 is aligned with the through-holes 98 in the first and second members 92 and 94 of the pivotal portion 84 of the pivotal jaw 80. is A pivot pin 272 (FIG. 1) is inserted through the aligned through holes 98 and 140 and is secured to the first and second members 92 and 94 of the pivotal portion 84 of the pivotal jaw 80. The pivot pin 272 enables the pivotal jaw 80 to pivot relative to the actuator shaft 106.

Next, each of the pivot elements 100 of the pivotal jaw 80 is inserted into the opening of a respective slot 54 and 56 that is open on the first axial end 22 of the fixed shaft 16. With the actuator shaft 106 angled upwardly away from the fixed shaft 16, as shown in FIG. 14, the pivotal jaw 80 is moved toward the second axial end 24 of the fixed shaft 16. The pivotal jaw 80 is moved into the position shown in FIG. 14 in which each of the pivot elements 100 is located adjacent the through-hole 50 and 52 of the slot 54 and 56, respectively, near the second axial end 24 of the fixed shaft 16. The first axial end 22 of the fixed shaft 16 is then inserted into the widened portion 180 of the fixed handle 150 and the fixed shaft 16 is secured, for example by welding, to the fixed handle 150. After securing the fixed shaft 16 to the fixed handle 150, the actuator shaft 106 is moved downwardly from the position shown in FIG. 14 to the position shown in FIG. 15. During the downward movement of the actuator shaft 106, the pivotal jaw 80 is forced upwardly so that the pivot elements 100 of the pivotal jaw 80 become located in the through-holes 50 and 52. When located in the through-holes 50 and 52, the pivot elements 100 of the pivotal jaw 80 are prevented from moving axially relative to the fixed shaft 16. The pivotal jaw 80 and the fixed jaw 20, when connected together as shown in FIG. 15, collectively form a clamp 280.

The actuator shaft 106, when moved downwardly into the position shown in FIG. 15, is received within the channel 48 of the fixed shaft 16. When received in the channel 48 of the fixed shaft 16, the end surfaces 128 of the side walls 114 and 116 of the actuator shaft 106 rest on the first and second end surfaces 38 and 40 of the bottom wall 26 of the fixed shaft 16. The outer surfaces 126 of the side walls 114 and 116 of the actuator shaft 106 lie in the channel 48 of the fixed shaft 16 adjacent the inner surfaces 42 of the first and second side walls 28 and 30 of the fixed shaft 16. When the actuator shaft 106 is lying adjacent the fixed shaft 16 as shown in FIG. 15, the point 122 of the actuator shaft 106 and the point 36 of the fixed shaft 16 align on a central axis of a cylindrical passage 290 that is formed between the actuator shaft 106 and the fixed shaft 20.

When the actuator shaft 106 is moved downwardly into the channel 48 of the fixed shaft 16, the first linking element 130 of the actuator shaft 106 is received in the channel 164 of the fixed handle 150. The actuator shaft 106 is moved axially to align the through-hole 136 in the linking member 134 of the first linking element 130 with the through-holes 174 and 176 extending into the slots 170 and 172 in the fixed handle 150. The actuator handle 200 is then inserted into the channel 164 in the fixed handle 150 so that the linking member 134 of the first linking element 130 of the actuator shaft 106 is received in the channel 214 between the first and second flanges 216 and 218 of the actuator handle 200. The actuator handle 200 is moved to align the coaxial through-holes 222 adjacent the second axial end 212 of the actuator handle 200 with the through-hole 136 in the linking member 134 of the first linking element 130 of the actuator shaft 106 and the through-holes 174 and 176 of the fixed handle 150. A pivot pin 274 (FIG. 1) is then inserted through one of the through-holes 174 and 176 in the fixed handle 150 and into the though-holes 222 and 136 in the actuator handle 200 and the first linking element 130, respectively. When properly inserted, one end of the pivot pin 274 is located in the slot 170 of the side wall 160 of the fixed handle 150 and the other end of the pivot pin 274 is located in the slot 172 of the side wall 162 of the fixed handle 150. A center portion of the pivot pin 274 enables pivotal movement of the actuator handle 200 relative to the actuator shaft 106 about the pivot pin 274 while the ends of the pivot pin 274 are retained within the slots 170 and 172 of the fixed handle 150.

The second axial end 234 of the actuator linkage 230 is then inserted into the channel 214 of the actuator handle 200 and the through-hole 236 of the second axial end 234 of the actuator linkage 230 is aligned with the coaxial through-holes 220 adjacent the first axial end 210 of the actuator handle 200. A pivot pin 276 (FIG. 1) is inserted into the aligned through-holes 236 and 220 and is secured to the first and second flanges 216 and 218 of the actuator handle 200. The pivot pin 276 enables pivotal movement between the actuator linkage 230 and the actuator handle 200.

The through-hole 238 in the first axial end 232 of the actuator linkage 230 is then aligned with the through-holes 166 and 168 in the upper portions of the side walls 160 and 162 of the fixed handle 150. A pivot pin 278 (FIG. 1) is inserted into the aligned through-holes 238, 166, and 168 and is secured to the upper portions of the side walls 160 and 162 of the fixed handle 150. The pivot pin 278 enables pivotal movement of the actuator linkage 230 relative to the fixed handle 150 for opening and closing the clamp 280 of the reduction device 12.

Figure 21:
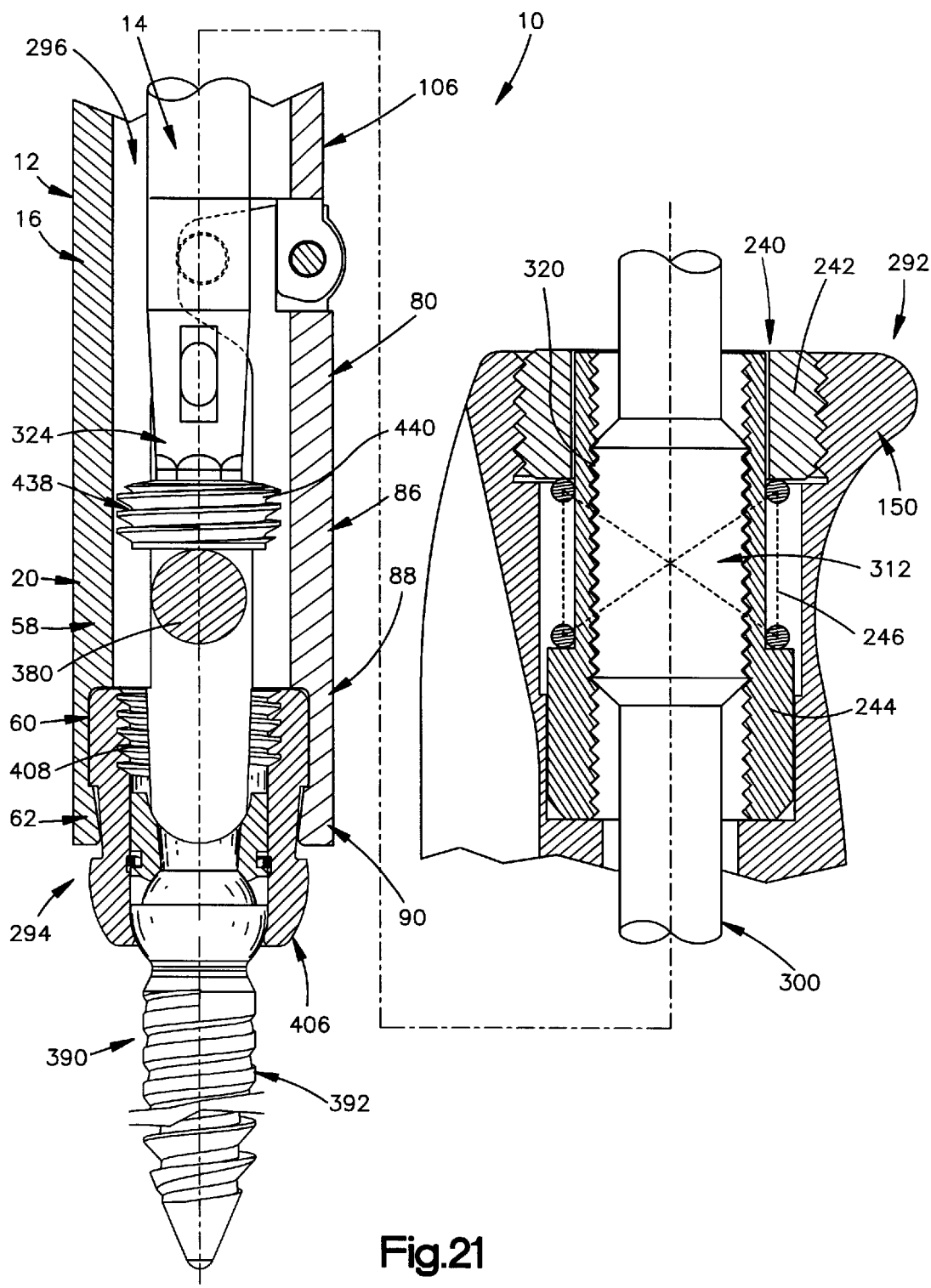
FIG. 21 illustrates a cross-sectional view of a portion of the surgical instrument of FIG. 1 being used in conjunction with the fastener of FIG. 21.

The translating mechanism 240 is then assembled into the fixed handle 150. To assemble the translating mechanism 240 in the fixed handle 150, the carriage 244 is inserted, head portion 258 first, through the first and second cylindrical bores 182 and 184 adjacent the first axial end 152 of the fixed handle 150 and into the non-cylindrical bore 186. When the head portion 258 of the carriage 244 is located in the non-cylindrical bore 186, the interaction between the planar surfaces 266 of the head portion 258 of the carriage 244 and the planar surfaces 196 and 198 defining the non-cylindrical bore 186 prevent the carriage 244 from rotating relative to the fixed handle 150. When the head portion 258 of the carriage 244 is located in the non-cylindrical bore 186, the slider portion 256 of the carriage 244 extends through the second cylindrical bore 184 and at least partially through the first cylindrical bore 182. FIG. 21 illustrates the slider portion 256 extending completely through the first cylindrical bore 182 to a position adjacent the first axial end 152 of the fixed handle 150.

The spring 246 is then placed around the slider portion 256 of the carriage 244 and is moved into contact with the head portion 258 of the carriage 244. The locking cap 242 is then screwed into the first cylindrical bore 182 and is locked in place with a substance such as LOCTITE®. When screwed into the first cylindrical bore 182, the locking cap 242 compresses the spring 246 to urge the carriage 244 to an end of the non-cylindrical bore 186 opposite the first axial end 152 of the fixed handle 150. The compressed spring 246 applies a predetermined axial load against the carriage 244 to prevent axial movement, or translation, of the carriage 244 toward the first axial end 152 of the fixed handle 150.

The assembled reduction device 12 includes a proximal end 292 and a distal end 294. The proximal end 292 is located at the first axial end 152 of the fixed handle 150 and the distal end 294 is located at the clamp 280. A lumen 296 (FIG. 16) extends axially through the reduction device 12 from the proximal end 292 to the distal end 294. The bore 268 in the carriage 244 of the translating mechanism 240, the bore 178 in the fixed handle 150, and the passage 290 formed by the actuator shaft 106 and fixed shaft 16 define the lumen 296. The threaded surface 270 defining the bore 268 in the carriage 244 forms a threaded portion of the lumen 296.

The drive device 14 (FIG. 1) includes a driver 300 and a driver spring 302. The driver extends axially along axis A and includes first and second axial end portions 304 and 306, respectively, and an intermediate portion 308. The intermediate portion 308 of the driver 300 is a cylindrical shaft.

The first axial end portion 304 of the driver 300 includes a tool receiving portion 310 and a drive portion 312. A cylindrical shaft 314 interconnects the tool receiving portion 310 and the drive portion 312. The tool receiving portion 310 of the driver 300 is hexagonal and includes an annular recess 316 for locking a drive tool (not shown) to the driver 300. An end surface 318 (FIG. 16) of the tool receiving portion 310 forms a first axial end of the driver 300. The drive portion 312 of the first axial end portion 304 of the driver 300 is cylindrical and has a larger diameter than the remainder of the driver 300. The outer surface 320 of the drive portion 312 is threaded.

The second axial end portion 306 of the driver 300 includes a centering portion 322 and a drive portion 324. A cylindrical shaft 326 interconnects the centering portion 322 and the drive portion 324. The centering portion 322 of the driver 300 is cylindrical and has a diameter that is larger than the shaft 326 and is smaller than the drive portion 312 of the first axial end portion 304 of the driver 300. The drive portion 324 of the second axial end portion 306 of the driver 300 is hexagonal. An end surface 328 (FIG. 12) of the drive portion 324 forms a second axial end of the driver 300.

As shown in FIG. 12, a cylindrical bore 330 extends into the end surface 328 at the second axial end of the driver 300. The bore 330 extends axially through the drive portion 324 and partially into the shaft 326 of the second axial end portion 306 of the driver 300. A window 332 extends radially through the shaft 326 of the second axial end portion 306 of the driver 300 and connects to the bore 330.

As shown in FIG. 12, the driver spring 302 includes a stepped shaft 340 and a head portion 342. The stepped shaft 340 includes first and second tubular portions 344 and 346, respectively. The first tubular portion 344 forms a first axial end of the driver spring 302 and connects to the second tubular portion 346. The second tubular portion 346 has an outer diameter that is slightly larger than an outer diameter of the first tubular portion 344. The inner diameters of the first and second tubular portions are the same and collectively form a passage 348 through the stepped shaft 340.

The head portion 342 of the driver spring 302 is connected to the second tubular portion 346 of the stepped shaft 340, opposite the first tubular portion 344. As shown in FIG. 13, the head portion 342 of the driver spring 302 is generally square and includes four side surfaces 350 and an end surface 352. Corners 354, connecting adjacent side surfaces 350, are rounded. The side surfaces 350 and the corners 354 taper radially inwardly toward the end surface 352. The taper of the corners 354 is greater than the taper of the side surfaces 350 so that the end surface 352 is generally circular.

An opening 356 extends through the center of the head portion 342 and connects to the passage 348 of the stepped shaft 340. The diameter of the opening 356 is the same as the inner diameters of the first and second tubular portions 344 and 346 of the stepped shaft 340.

Four grooves 358 extend axially through the head portion 342 and through a portion of the second tubular portion 346 of the driver spring 302. FIG. 12 shows one groove 358 extending axially through a portion of the second tubular portion 346 of the driver spring 302. In the head portion 342 of the driver spring 302, the four grooves 358 extend radially between the opening 356 and the side surfaces 350, as shown in FIG. 13. In the second tubular portion 346 of the driver spring 302, the four grooves 358 extend between the inner diameter and the outer diameter. Each side surface 350 of the head portion 342 has an associated groove 358. The associated groove 358 extends through the center of the side surface 350. The four grooves 358 enable the head portion 342 of the driver spring 302 to be compressed radially inwardly when subjected to a radially inwardly directed force. The head portion 342 resiliently returns to its original shape when the radially inwardly directed force is removed.

To assemble the drive device 14, the first tubular portion 344 of the driver spring 302 is inserted into the bore 330 on the second axial end of the driver 300. When the head portion 342 of the driver spring 302 is near the second axial end of the driver 300, the first tubular portion 344 of the driver spring 302 is fixed to the driver 300. Preferably, the first tubular portion 344 of the driver spring 302 is either soldered to or welded to the driver 300 with access to the first tubular portion 344 being provided through the window 332.

The surgical instrument 10 of the present invention may be used for moving a vertebra relative to another vertebra, preferably along the sagittal plane of a body 360 during a surgical procedure. The surgical procedure may include open surgery. Preferably, the surgical procedure is performed through a cannula 368.

FIG. 19 illustrates three vertebrae 362, 364 and 366. Vertebra 364 is moved or slipped along the sagittal plane of the body 360 relative to vertebrae 362 and 364. FIG. 19 also illustrates the cannula 368 having an expandable distal end or skirt portion 370. An exemplary cannula is disclosed in U.S. Pat. No. 6,187,000 B1, which is incorporated herein by reference in its entirety. The cannula 368 provides a passage into the body 360. The expanded skirt portion 370 of the cannula 368 defines an operative space that provides access to all three vertebrae 362, 364 and 366. An endoscope (not shown) may be extended through the cannula 368 for providing vision within the operative space.

FIG. 20 illustrates a surgically implantable longitudinal member or rod 380 for maintaining bone portions, such as vertebrae of a spinal column, in a desired spatial relationship. The rod 380 is made of a suitable biocompatible material. The rod 380 illustrated in FIG. 20 has a length that is sufficient to span the three vertebrae 362, 364, and 366. The length of the rod 380 in any particular installation will depend upon the condition to be corrected and the number of vertebrae to be held in a desired spatial relationship relative to each other by the rod 380.

Fasteners 390 connect the rod 380 with vertebrae of the spinal column. Each fastener 390 is made of a suitable biocompatible material. Each fastener 390 illustrated in FIG. 20 is identical. Therefore, only one of the fasteners 390 is described in detail.

Figure 17:
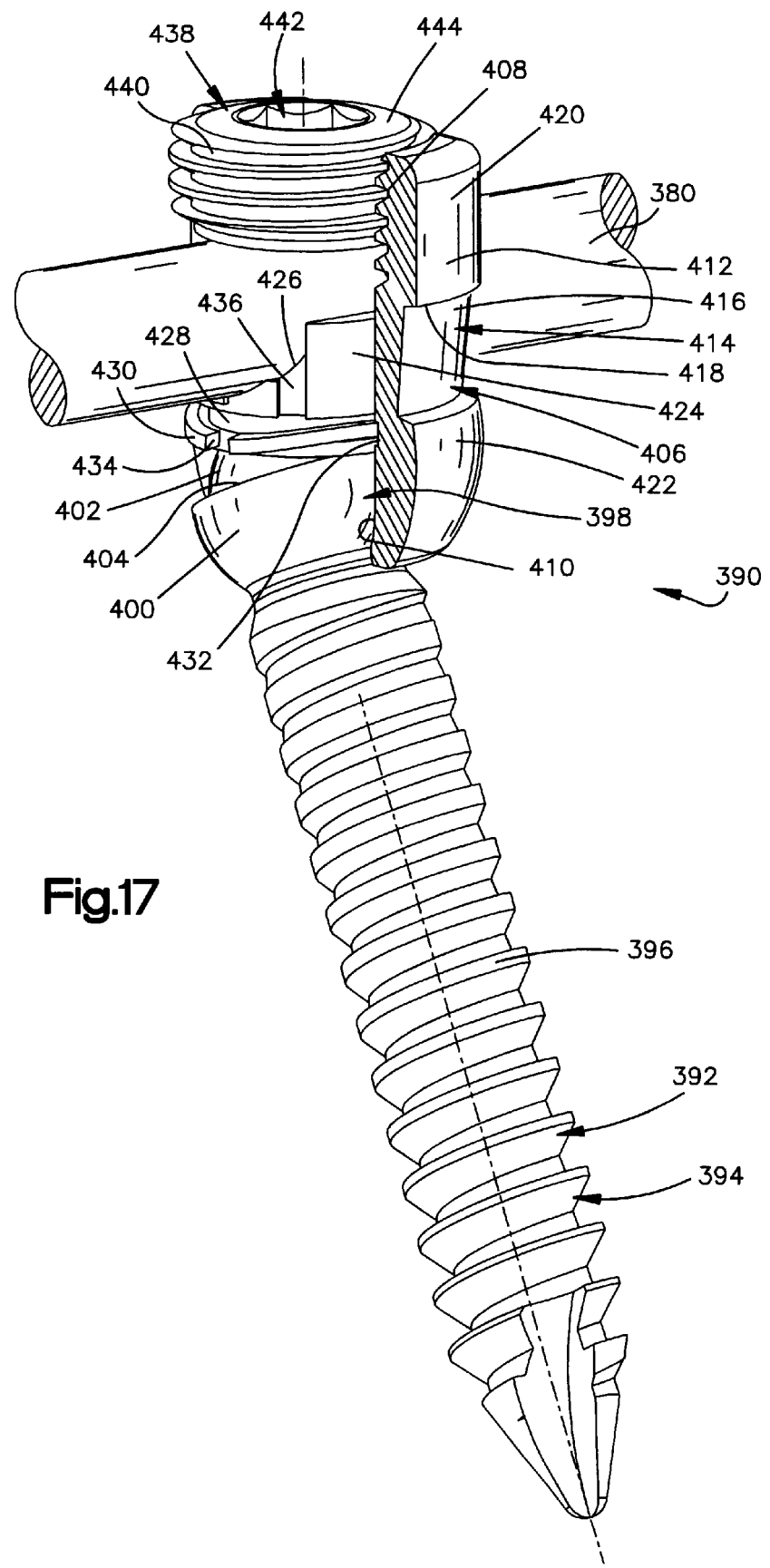
FIG. 17 is a perspective view, partially in section, of a fastener for use with the surgical instrument of FIG. 1.

With reference to FIG. 17, the fastener 390 includes a shank 392. The shank 392 has a threaded portion 394 having a course thread convolution 396 for engaging the vertebra. A head portion 398 of the shank 392 is provided with first and second spherical surfaces 400 and 402, respectively. The second spherical surface 402 has a diameter less than a diameter of the first spherical surface 400. A radially extending shoulder 404 extends between the first and second spherical surfaces 400 and 402. A recess (not shown) is provided in the second spherical surface 402 of the head portion 398 of the shank 392 for receiving a tool (not shown) that applies torque to the shank 392 to turn the thread convolution 396 into a vertebra.

The shank 392 extends into a housing 406 of the fastener 390 that interconnects the rod 380 and the shank 392. The housing 406 has a laterally extending passage through which the rod 380 extends and a longitudinal passage that extends transverse to the lateral passage and intersects the lateral passage within the housing 406. The longitudinal passage includes a top opening defined by a threaded inner surface 408 and a lower opening that is defined by a concave inner surface 410. The shank 392 is inserted through the top opening in the housing 406 and the threaded portion 394 of the shank 392 extends outwardly of the housing 406 through the lower opening. The first spherical surface 400 of the shank 392 engages a concave spherical surface 410 of the housing 406 adjacent the narrow opening. Accordingly, the shank 392 is pivotal relative to the housing 406 into a plurality of angular positions.

An outer surface 412 of the housing 406 includes a circumferentially extending groove 414 that includes a smooth bottom surface 416. A radially outwardly extending shoulder 418 defines an upper side wall of the groove 414 and connects to an upper rim surface 420. An arced lower rim surface 422 defines a lower side wall of the groove 414.

A spacer 424 is received in the longitudinal passage of the housing 406. The spacer 424 has a concave spherical bottom surface (not shown) that engages the second spherical surface 402 of the shank 392. The shoulder 404 on the shank 392 engages the spacer 424 to limit the relative movement between the shank 392 and the housing 406. The spacer 424 also has a concave cylindrical upper surface 426 that engages the rod 380. An opening (not shown) extends through the spacer 424 to receive the tool (not shown) that engages the recess in the shank 392.

The spacer 424 has a circumferential groove 428 for receiving a compressible member such as a spring member 430. An inner surface of the housing 406 includes a circumferential groove 432 for receiving the spring member 430 so that the spring member 430 extends from the groove 428 in the spacer 424, to the groove 432 in the housing 406. The spring member 430 is a ring having a gap 434 that permits radial contraction and expansion of the spring member 430.

The spring member 430 urges the spacer 424 axially toward the shank 392 to press the housing 406 against the first spherical surface 400 of the shank 392. The spherical bottom surface of the spacer 424 frictionally engages the second spherical surface 402 of the shank 392 and the first spherical surface 400 of the shank 392 frictionally engages the housing 406. The shank 392 and the housing 406 are manually movable relative to each other by a surgeon when the rod 380 is disengaged from the spacer 324.

The spacer 324 has four axially extending slots 436, one of which is shown in FIG. 17. The slots 436 intersect the groove 428. A tool (not shown) having four prongs may be extended through the slots 436 and into engagement with the spring member 430. The tool grasps the spacer 424 and the spring member 430 for inserting the spacer 424 and the spring member 430 into the housing 406. The prongs of the tool engage the spring member 430 to radially contract the spring member 430 into the groove 428 in the spacer 424. The prongs hold the spring member 430 in the radially contracted condition in the groove 428 while the spacer 424 and spring member 430 are inserted into the housing 406. Once the spacer 424 engages the shank 392, the prongs are removed from the slots 436 and the spring member 430 radially expands into the groove 432 in the housing 406. Although the spacer 424 is described as having four slots 436, the spacer 424 could have any number of slots 436 and the tool would have the same number of prongs as the spacer 424 has slots 436.

A threaded member or setscrew 438 having a threaded outer surface 440 is received in the threaded top opening of the housing 406. When screwed into the housing 406, the setscrew 438 engages the rod 380 and applies a force to the rod 380 to press the rod against the spacer 424 and the spacer against the shank 392. The setscrew 438 clamps the rod 380, the spacer 424, and the housing 406 to the shank 392 to prevent movement of the shank 392 relative to the housing 406. After the setscrew 438 secures the rod 380 relative to the housing 406, the shank 392 is no longer movable relative to the housing 406. Thus, the setscrew 438 locks the shank 392 and the housing 406 relative to one another.

FIG. 18 shows a partial cross-section of the setscrew 438 of the fastener 390. A hexagonal bore 442 extends into an upper surface 444 of the setscrew 438. The hexagonal bore 442 is sized to receive the drive portion 324 of the second axial end portion 306 of the driver 300. A cylindrical bore 446, which is defined by cylindrical surface 448, extends into the setscrew 438 below the hexagonal bore 442. The cylindrical bore 446 and the hexagonal bore 442 are coaxial. A diameter of the cylindrical bore 446 is less than a width across the hexagonal bore 442 and is also less than the distance between rounded corners 354 of the head portion 342 of the driver spring 302.

The driver spring 302 holds the setscrew 438 on the drive device 14. The hexagonal drive portion 324 of the driver 300 is adapted to fit in the hexagonal bore 442 of the setscrew 438. When the drive portion 324 of the driver 300 is received in the hexagonal bore 442 of the setscrew 438, the driver spring 402 is received in the cylindrical bore 446 of the setscrew 438 for holding the setscrew on the drive device 14.

FIG. 18 illustrates the driver spring 302 holding the setscrew 438 on the drive device 14. When inserted into the cylindrical bore 446 of the setscrew 438, the side surfaces 350 of the driver spring 302 are forced together. The grooves 358 of the driver spring 302 enable the side surfaces 350 to move toward one another during axial movement of the driver spring 302 into the cylindrical bore 446. The four rounded corners 354 of the driver spring 302 press radially outwardly into contact with the cylindrical surface 448 defining the cylindrical bore 446 to hold the setscrew 438 on the drive device 14. To remove the setscrew 438 from the driver spring 302, the setscrew 438 is pulled axially off of the driver spring 302. The force of the driver spring 302 holding the setscrew 438 is sufficient to enable the setscrew 438 to be held vertically below the drive device 14.

As shown in FIG. 19, fasteners 390 are secured in each of the vertebrae 362, 364, and 366. The rod 380 extends between vertebrae 362 and 366 and is locked in place relative to vertebrae 362 and 366. As shown in FIG. 20, the housing 406 attached to the shank 392 of the fastener 390 secured in vertebra 364 is spaced, along the sagittal plane of the body 360, from the rod 380. The surgical instrument 10 of the present invention moves vertebra 364 along the sagittal plane of the body 360 and relative to vertebrae 362 and 366 so that the fastener 390 attached to vertebra 364 may be fastened to the rod 380.

To move vertebra 364 along the sagittal plane of the body 360, the distal end 294 of the reduction device 12 is inserted into the body 360 through the passage of the cannula 368. When the distal end 294 of the reduction device 12 is located in the operative space, the actuator handle 200 is pivoted away from the fixed handle 150 to move the actuator shaft 106 toward the proximal end 292 of the reduction device 12 and pivot the pivotal jaw 80 into an open position opening the clamp 280. The distal end 294 of the reduction device 12 is moved within the operative space to a position in which the rod 380 is located adjacent the inner surface 64 of the linking portion 58 of the fixed jaw 20 and the gripping portion 62 of the fixed jaw 20 is positioned in the circumferential groove 414 of the housing 406 attached to vertebra 364. When the gripping portion 62 of the fixed jaw 20 is positioned in the circumferential groove 414, the upper rim surface 420 of the housing 406 is received in the mouth portion 60 of the fixed jaw 20.

The actuator handle 200 is then pivoted toward the fixed handle 150 of the reduction device 12. As a result, the actuator shaft 106 is moved toward the distal end 294 of the reduction device 12 and the pivotal jaw 80 is closed or pivoted toward the fixed jaw 20 to close the clamp 280. During closure of the clamp 280, the distal end 294 of the reduction device 12 is manipulated so that the gripping portion 90 of the pivotal jaw 80 is positioned in the circumferential groove 414 of the housing 406 opposite to the gripping portion 62 of the fixed jaw 20 and the upper rim surface 420 of the housing 406 is received in the mouth portion 88 of the pivotal jaw 80 opposite the mouth portion 60 of the fixed jaw 20. Thus, when the actuator handle 200 is pivoted toward the fixed handle 150, the housing 406 attached to vertebra 364 becomes locked in the clamp 280 formed between the fixed and pivotal jaws 20 and 80 of the reduction device 12 with the rod 380 located between the linking portions 58 and 86 of the fixed and pivotal jaws 20 and 80, respectively.

The second axial end of the drive device 14, with a setscrew 438 attached to the driver spring 302, is then inserted into the lumen 296 of the reduction device 12 and is moved toward the distal end 294 of the reduction device until the threaded drive portion 312 of the driver 300 engages the threaded inner surface 270 of the carriage 244. A tool (not shown), such as a T-handle ratchet, attached to the tool receiving portion 310 of the driver 300 is manipulated to rotate the drive device 14. During rotation of the drive device 14, the threaded drive portion 312 of the driver 300 engages the threaded inner surface 270 of the carriage 244 and results in the drive device 14 moving axially along the lumen 296 and relative to the carriage 244 of the reduction device 12.

Figure 24:
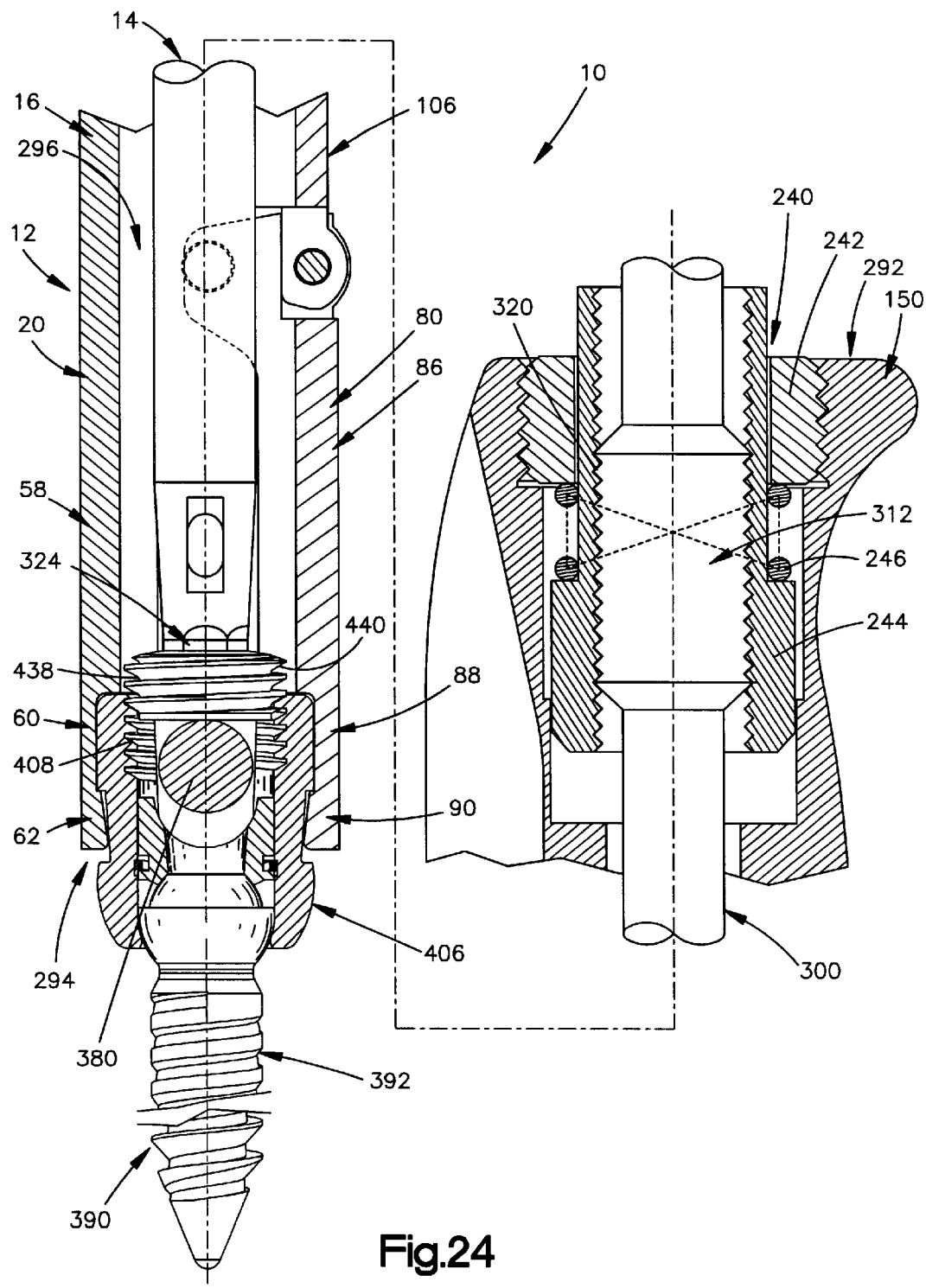
FIG. 24 is a cross-sectional view of a portion of the surgical instrument of FIG. 1 inserting a setscrew into the fastener of FIG. 17 to secure a vertebra to a rod.

The drive device 14, which is holding on the setscrew 438, presses the setscrew 438 against the rod 380. Rotation of the drive device 14 relative to the reduction device 12 and within the carriage 244 results in an axially directed drive force that tends to move the fastener 390 in vertebra 364 toward rod 380. When the force necessary to move vertebra 364 relative to vertebrae 362 and 366 is less than the axially directed drive force and is less than the predetermined axial load of the spring 246 on the carriage 244, relative rotation between the reduction device 12 and the drive device 14 moves vertebra 364 relative to vertebrae 362 and 366. Thus, when the drive force is less than the spring force, the clamp 280 of the reduction device 12, which is clamped to the fastener 390 fixed to vertebra 364, is moved relative to the drive device 14 during rotation of the drive device relative to the reduction device 12 so that the fastener 390 fixed to vertebra 364 is moved closer to the rod 380. During this movement, the carriage 244 is stationary relative to the fixed handle 150. Continued rotation of the drive device 14 relative to the reduction device 12, moves vertebra 364 relative to vertebrae 362 and 366 and into a position in which the rod 380 is partially received in the housing 406 of the fastener 390 fixed to vertebra 364 and the threaded surface 408 of the housing 406 is brought into contact with the threaded outer surface 440 of the setscrew 438, as shown in FIG. 24.

When the drive force is greater than the predetermined axial load of spring 246 on carriage 244, rotation of the drive device 14 relative to the reduction device 12 moves the carriage 244 of the translating mechanism 240 toward the cap 242 causing the spring 246 to be compressed. Since the interaction between the planar surfaces 266 of the head portion 258 of the carriage 244 and the planar surfaces 196 and 198 defining the non-cylindrical bore 186 prevent the carriage 244 from rotating relative to the fixed handle 150 of the reduction device 12, rotation of the drive device 14 relative to the reduction device 12 results in only translation or axial movement of the carriage 244 relative to the fixed handle 150. Thus, when the drive force is greater than the spring force, the translation of the carriage 244 results in rotation of the drive device 14, and thus the setscrew 438, relative to the reduction device 12 without any relative axial movement between the drive device 14 and the clamp 280 of the reduction device 12. As the spring 246 of the translation device 240 is compressed, the spring force or predetermined axial load increases. When the spring force becomes greater than the drive force, the drive force again acts to move the drive device 14 axially relative to the clamp 280 of the reduction device 12.

When the threaded outer surface 440 of the setscrew 438 contacts the threaded inner surface 408 of the housing 406 of the fastener 390 fixed to vertebra 364, an interaction between the threads of the threaded surfaces 408 and 440 may resist further relative axial movement between vertebra 364 and vertebrae 362 and 366. As a result, the drive force necessary to continue axial movement of vertebra 364 relative to vertebrae 362 and 366 increases. If the drive force remains below the spring force, relative rotation between the drive device 14 and the reduction device 12 results in rotation of the setscrew 438 relative to the housing 406 and moves the setscrew 438 axially into the housing 406 to lock vertebra 364 relative to the rod 380.

Misalignment of the threaded outer surface 440 of the setscrew 438 and the threaded inner surface 408 of the housing 406 may result in the drive force increasing above the spring force. When the drive force becomes greater than the spring force, further rotation of the drive device 14 relative to the reduction device 12 results in axial movement of the carriage 244 away from vertebra 364 and toward cap 242. As a result of the axial movement of the carriage 244, relative rotation between the drive device 14 and the reduction device 12 results in the setscrew 438 rotating relative to the housing 406 of the fastener 390 fixed to vertebra 364 but does not cause any translation or relative axial movement between the setscrew 438 and the housing 406. Rotation of the setscrew 438 without translation of the setscrew relative to the housing 406 enables proper alignment of the threaded surfaces 440 and 408 of the setscrew 438 and the housing 406 before the setscrew is screwed or threaded into the housing. As a result, cross-threading between the setscrew 438 and the housing 406 is prevented. When the threaded surfaces 440 and 408 of the setscrew 438 and the housing 406 are properly aligned, rotation of the drive device 14 screws or threads the setscrew 438 into the housing 406 to secure vertebra 364 to the rod 380.

Figure 25:
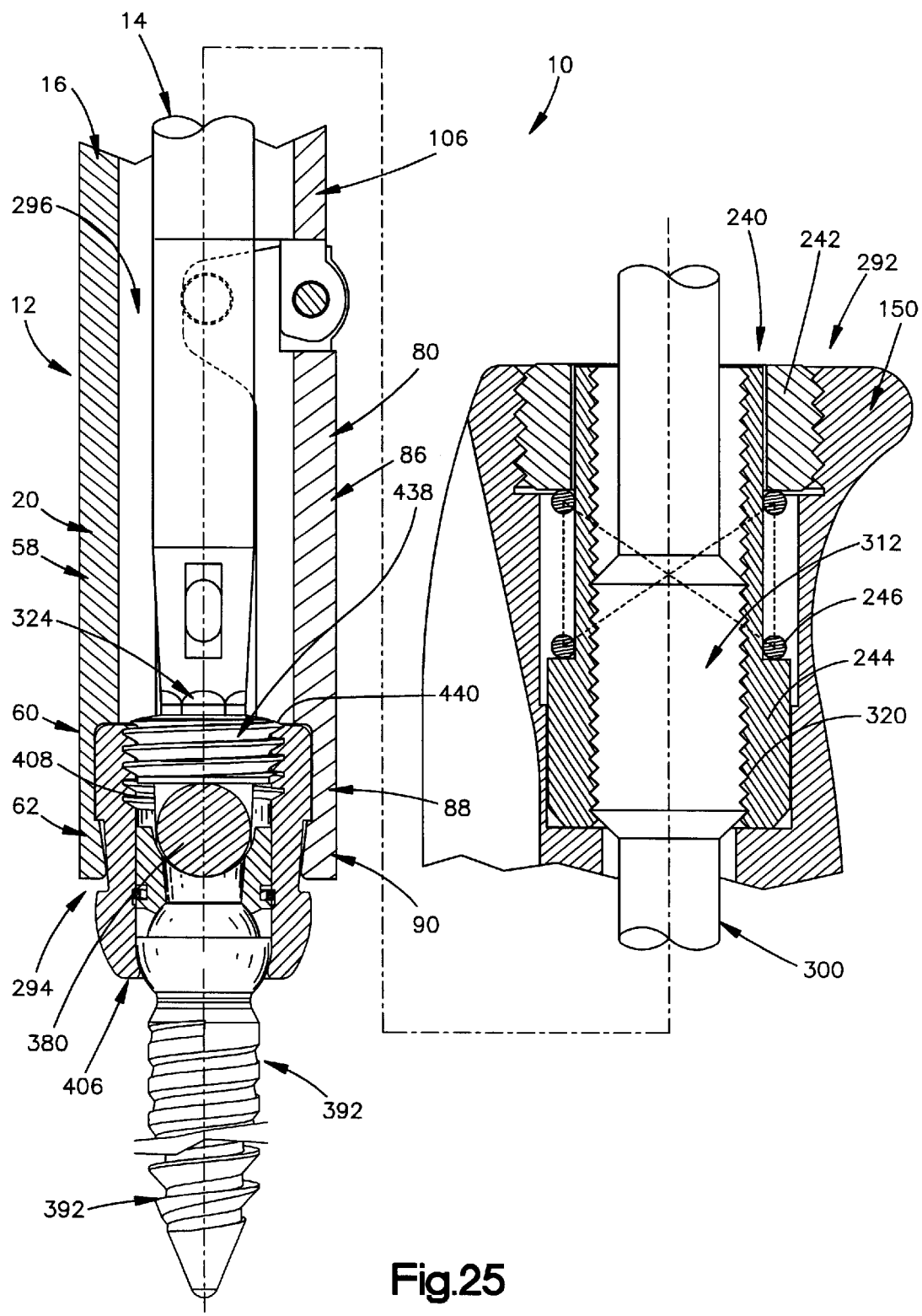
FIG. 25 is a cross-sectional view of a portion of the surgical instrument of FIG. 1 after complete insertion of the setscrew into the fastener of FIG. 17 to secure a vertebra to a rod.

When the setscrew 438 is secured in the housing 406 and vertebra 364 is secured to the rod 380, as is shown in FIG. 25, the drive device 14 is pulled upwardly and out of the proximal end 292 of the reduction device 12. The actuator handle 200 of the reduction device 12 is then moved away from the fixed handle 150 to pivot the pivotal jaw 80 and open the clamp 280. The reduction device 12 may then be removed from the housing 406 of the fastener 390, and removed from the cannula 368. Then, the cannula 368 may be removed from the body 360 and the body may be sutured in an appropriate manner.

From the above description of the invention, those skilled in the art will perceive improvements, changes and modifications. Such improvements, changes and modifications within the skill of the art are intended to be covered by the appended claims.

Having described the invention, I claim the following:

1. A surgical instrument for moving a first bone portion relative to a second bone portion, the surgical instrument comprising:

a first device including an actuatable clamp for clamping on a fastener fixed to the first bone portion and a threaded carriage that is movable axially relative to the clamp in a direction away from the first bone portion when subjected to a predetermined axial load; and a second device including a threaded portion adapted for threaded engagement with the carriage of the first device and an end portion for supporting a member which engages the fastener fixed to the first bone portion and secures a rod connected to the second bone portion to the fastener, the end portion being adapted for pressing the member against the rod, relative rotation between the first and second devices during threaded engagement of the carriage of the first device and the threaded portion of the second device causing relative axial movement between the second device and the carriage of the first device, the carriage being stationary relative to the clamp of the first device when a force necessary to produce relative movement between the first and second bone portions is below the predetermined axial load so that relative rotation between the first and second devices moves the clamp and the fastener that is fixed to the first bone portion and the first bone portion relative to the second bone portion and relative to the rod.

2. The surgical instrument of claim 1 wherein the carriage moves axially away from the first bone portion and relative to the clamp of the first device when the force necessary to produce relative movement between the first and second bone portions exceeds the predetermined axial load so that the first and second bone portions are not moved in response to relative rotation between the first and second devices.

3. The surgical instrument of claim 2 wherein the member supported on the end portion of the second device is rotated relative to the fastener clamped by the clamp of the first device but is not moved axially relative to the fastener when the carriage moves axially away from the first bone portion and relative to the clamp.

4. The surgical instrument of claim 1 wherein the clamp is actuatable between open and closed positions, the clamp including first and second clamping portions, the first clamping portion being pivotal relative to the second clamping portion in response to movement of an actuator handle.

5. The surgical instrument of claim 4 wherein an actuator shaft connects the actuator handle and the first clamping portion, a fixed shaft connecting a fixed handle and the second clamping portion, the actuator shaft being moved relative to the fixed shaft in response to movement of the actuator handle relative to the fixed handle, movement of the actuator shaft relative to the fixed shaft pivoting the first clamping portion relative to the second clamping portion.

6. The surgical instrument of claim 5 wherein a pivot pin pivotally connects the actuator shaft to the actuator handle, the fixed handle including a pair of axially extending slots, each slot receiving an associated end portion of the pivot pin, the actuator shaft being axially movable relative to the fixed handle in response to movement of the actuator handle relative to the fixed handle.

7. The surgical instrument of claim 5 wherein the first clamping member is pivotally connected to the fixed shaft.

8. The surgical instrument of claim 4 wherein the first clamping portion is separated from the second clamping portion so that the rod may be received between the first and second clamping portions when the clamp is clamping the fastener fixed to the first bone portion.

9. The surgical instrument of claim 8 wherein the first device includes proximal and distal ends, the clamp being located at the distal end of the first device, a lumen extending through the first device between the proximal and distal ends for receiving the second device, a threaded bore extending through the carriage forming a threaded portion of the lumen.

10. The surgical instrument of claim 9 wherein the first device includes a fixed handle, the first clamping portion being pivoted in response to movement of the actuator handle relative to the fixed handle, a portion of the lumen extending through the fixed handle.

11. The surgical instrument of claim 10 wherein the fixed handle includes surfaces defining a non-cylindrical bore, the carriage having a non-cylindrical portion that is received in the non-cylindrical bore, the surfaces defining the non-cylindrical bore engaging the non-cylindrical portion of the carriage to prevent rotation of the carriage relative to the fixed handle during relative rotation between the first and second devices.

12. The surgical instrument of claim 11 wherein the fixed handle includes first and second axial ends, the first axial end of the fixed handle forming the proximal end of the first device, the fixed handle including a spring bore adjacent the non-cylindrical bore on a side nearer the first axial end of the fixed handle, a spring located in the spring bore urging the carriage toward the second axial end of the fixed handle, the spring being compressed during axial movement of the carriage away from the clamp.

13. The surgical instrument of claim 1 wherein the end portion of the second device includes a resilient component for supporting the member which engages the fastener, the member including a surface defining a bore for receiving the resilient component, the resilient component being radially compressed during insertion into the bore of the member and engaging the surface defining the bore of the member to support the member on the end portion of the second device.

14. A surgical instrument for moving a first bone portion of a body relative to a second bone portion of the body, the surgical instrument comprising:

a cannula for forming a passage into the body and for defining an operative space adjacent the first and second bone portions;

a first device that is extendable through the passage formed by the cannula, the first device including an actuatable clamp for clamping on a fastener fixed to the first bone portion and a threaded carriage that is movable axially relative to the clamp in a direction away from the first bone portion when subjected to a predetermined axial load; and a second device that is also extendable through the passage formed by the cannula, the second device including a threaded portion adapted for threaded engagement with the carriage of the first device and an end portion for supporting a member which engages the fastener fixed to the first bone portion and secures a rod connected to the second bone portion to the fastener, the end portion being adapted for pressing the member against the rod, relative rotation between the first and second devices during threaded engagement of the carriage of the first device and the threaded portion of the second device causing relative axial movement between the second device and the carriage of the first device, the carriage being stationary relative to the clamp of the first device when a force necessary to produce relative movement between the first and second bone portions is below the predetermined axial load so that relative rotation between the first and second devices moves the clamp and the fastener fixed to the first bone portion and the first bone portion relative to the second bone portion and relative to the rod.

15. The surgical instrument of claim 14 wherein the carriage moves axially away from the first bone portion and relative to the clamp of the first device when the force necessary to produce relative movement between the first and second bone portions exceeds the predetermined axial load so that the first and second bone portion are not moved in response to relative rotation between the first and second devices.

16. The surgical instrument of claim 15 wherein the member supported on the end portion of the second device is rotated relative to the fastener clamped by the clamp of the first device but is not moved axially relative to the fastener when the carriage moves axially away from the first bone portion and relative to the clamp.

17. The surgical instrument of claim 14 wherein the clamp is actuatable between open and closed positions, the clamp including first and second clamping portions, the first clamping portion being pivotal relative to the second clamping portion in response to movement of an actuator handle.

18. The surgical instrument of claim 17 wherein an actuator shaft connects the actuator handle to the first clamping portion, a fixed shaft connecting a fixed handle and the second clamping portion, the actuator shaft being moved relative to the fixed shaft in response to movement of the actuator handle relative to the fixed handle, movement of the actuator shaft relative to the fixed shaft pivoting the first clamping portion relative to the second clamping portion.

19. The surgical instrument of claim 18 wherein the first clamping portion is separated from the second clamping portion so that the rod may be received between the first and second clamping portions when the clamp is clamping the fastener fixed to the first bone portion.

20. The surgical instrument of claim 19 wherein the first device includes proximal and distal ends, the clamp being located at the distal end of the first device, a lumen extending through the first device between the proximal and distal ends for receiving the second device, a threaded bore extending through the carriage forming a threaded portion of the lumen.

21. The surgical instrument of claim 20 wherein the first device includes a fixed handle, the first clamping portion being pivoted in response to movement of the actuator handle relative to the fixed handle, a portion of the lumen extending through the fixed handle.

22. The surgical instrument of claim 21 wherein the fixed handle includes surfaces defining a non-cylindrical bore, the carriage having a non-cylindrical portion that is received in the non-cylindrical bore, the surfaces defining the non-cylindrical bore engaging the non-cylindrical portion of the carriage to prevent rotation of the carriage relative to the fixed handle during relative rotation between the first and second devices.

23. The surgical instrument of claim 22 wherein the fixed handle includes first and second axial ends, the first axial end of the fixed handle forming the proximal end of the first device, the fixed handle including a spring bore adjacent the non-cylindrical bore on a side nearer the first axial end of the fixed handle, a spring located in the spring bore urging the carriage toward the second axial end of the fixed handle, the spring being compressed during axial movement of the carriage away from the clamp.

24. The surgical instrument of claim 14 wherein the end portion of the second device includes a resilient component for supporting the member which engages the fastener, the member including a surface defining a bore for receiving the resilient component, the resilient component being radially compressed during insertion into the bore of the member and engaging the surface defining the bore of the member to support the member on the end portion of the second device.

25. A surgical instrument for threadedly connecting a member and a fastener, the surgical instrument comprising:

a first device including an actuatable clamp for clamping on the fastener and a threaded carriage that is movable axially relative to the clamp in a direction away from the fastener when subjected to a predetermined axial load; and a second device including a threaded portion adapted for threaded engagement with the carriage of the first device and an end portion for supporting the member to be threadedly connected to the fastener, relative rotation between the first and second devices during threaded engagement of the carriage of the first device and the threaded portion of the second device causing relative axial movement between the second device and the carriage of the first device, the carriage moving axially away from the fastener that is clamped by the clamp of the first device when a force applied exceeds the predetermined axial load so that the member is rotated relative to the fastener but is not moved axially relative to the fastener in response to relative rotation between the first and second devices, the carriage being stationary relative to the fastener that is clamped by the clamp of the first device when the force applied is below the predetermined axial load so that relative rotation between the first and second devices results in the member being threadedly connected to the fastener.

26. The surgical instrument of claim 25 wherein the clamp is actuatable between open and closed positions, the clamp including first and second clamping portions, the first clamping portion being pivotal relative to the second clamping portion in response to movement of an actuator handle.

27. The surgical instrument of claim 26 wherein an actuator shaft connects the actuator handle and the first clamping portion, a fixed shaft connecting a fixed handle and the second clamping portion, the actuator shaft being moved relative to the fixed shaft in response to movement of the actuator handle relative to the fixed handle, movement of the actuator shaft relative to the fixed shaft pivoting the first clamping portion relative to the second clamping portion.

28. The surgical instrument of claim 27 wherein a pivot pin pivotally connects the actuator shaft to the actuator handle, the fixed handle including a pair of axially extending slots, each slot receiving an associated end portion of the pivot pin, the actuator shaft being axially movable relative to the fixed handle in response to movement of the actuator handle relative to the fixed handle.

29. The surgical instrument of claim 27 wherein the first clamping member is pivotally connected to the fixed shaft.

30. The surgical instrument of claim 27 wherein the fixed handle includes surfaces defining a non-cylindrical bore, the carriage having a non-cylindrical portion that is received in the non-cylindrical bore, the surfaces defining the non-cylindrical bore engaging the non-cylindrical portion of the carriage to prevent rotation of the carriage relative to the fixed handle during relative rotation between the first and second devices.

31. The surgical instrument of claim 30 wherein the fixed handle includes first and second axial ends, the first axial end of the fixed handle forming the proximal end of the first device, the fixed handle including a spring bore adjacent the non-cylindrical bore on a side nearer the first axial end of the fixed handle, a spring located in the spring bore urging the carriage toward the second axial end of the fixed handle, the spring being compressed during axial movement of the carriage away from the clamp.

32. The surgical instrument of claim 25 wherein the end portion of the second device includes a resilient component for supporting the member, the member including a surface defining a bore for receiving the resilient component, the resilient component being radially compressed during insertion into the bore of the member and engaging the surface defining the bore of the member to support the member on the end portion of the second device.

* * * * *